US011338003B2

(12) United States Patent
Kuan

(10) Patent No.: US 11,338,003 B2
(45) Date of Patent: May 24, 2022

(54) METHODS OF TREATING BLADDER CANCER WITH AN ONCOLYTIC VIRUS

(71) Applicant: CG Oncology, Inc., Irvine, CA (US)

(72) Inventor: Arthur Kuan, Newport Coast, CA (US)

(73) Assignee: CG ONCOLOGY, INC., Irvine, CA (US)

( * ) Notice: Subject to any disclaimer, the term of this patent is extended or adjusted under 35 U.S.C. 154(b) by 290 days.

(21) Appl. No.: 16/605,066

(22) PCT Filed: Apr. 13, 2018

(86) PCT No.: PCT/US2018/027549
§ 371 (c)(1),
(2) Date: Oct. 14, 2019

(87) PCT Pub. No.: WO2018/191654
PCT Pub. Date: Oct. 18, 2018

(65) Prior Publication Data
US 2021/0085734 A1 Mar. 25, 2021

Related U.S. Application Data

(60) Provisional application No. 62/500,729, filed on May 3, 2017, provisional application No. 62/485,805, filed on Apr. 14, 2017.

(51) Int. Cl.
| | | |
|---|---|---|
| C12N 7/00 | (2006.01) | |
| A61K 35/761 | (2015.01) | |
| A61K 35/76 | (2015.01) | |
| A61K 35/768 | (2015.01) | |
| A61K 9/00 | (2006.01) | |
| A61P 35/00 | (2006.01) | |

(52) U.S. Cl.
CPC .......... *A61K 35/761* (2013.01); *A61K 9/0034* (2013.01); *A61P 35/00* (2018.01); *A61K 35/76* (2013.01); *A61K 35/768* (2013.01); *C12N 7/00* (2013.01); *C12N 2710/10032* (2013.01); *C12N 2710/10332* (2013.01)

(58) Field of Classification Search
None
See application file for complete search history.

(56) References Cited

U.S. PATENT DOCUMENTS

| 2915/0190505 | 7/2015 | Yeung |
|---|---|---|
| 2019/0070233 A1 | 3/2019 | Yeung |

FOREIGN PATENT DOCUMENTS

| EP | 2604110 A2 | 6/2013 |
|---|---|---|
| WO | 200200730 A2 | 1/2002 |
| WO | 200200730 A3 | 11/2002 |
| WO | 2010072900 A1 | 7/2010 |
| WO | 2016145354 A1 | 9/2016 |
| WO | 2017070110 A1 | 4/2017 |
| WO | 2017156349 A1 | 9/2017 |

OTHER PUBLICATIONS

Burke et al., The Journal of Urology, Dec. 2012, 188:2391-2397. (Year: 2012).*
Packiam et al., The Journal of Urology, May 6, 2016, 195(4S):e142. (Year: 2016).*
Ramesh et al., Clin Cancer Res, 2006, 12(1):305-313. (Year: 2006).*
Bassi, P. et al. (May 1999). "Prognostic Factors Of Outcome After Radical Cystectomy For Bladder Cancer: A Retrospective Study Of A Homogeneous Patient Cohort," Urol. 161(5):1494-1497.
Boehm, B.E. et al. (2015). "Novel Therapeutic Approaches for Recurrent Nonmuscle Invasive Bladder Cancer," Urol. Clin. N. Am. 42:159-168.
clinicaltrials.gov (Sep. 2011). "Efficacy Study of Recombinant Adenovirus for Non Muscle Invasive Bladder Cancer (BOND)," ClinicalTrials.gov Identifier: NCT01438112, retrieved from internet URL:https://clinicaltrials.gov/ct2/show/NCT0 1438112, last visited Jun. 15, 2018, 10 pages.
clinicaltrials.gov. (Feb. 19, 2019). "Safety and Efficacy of CG0070 Oncolytic Virus Regimen for High Grade NMIBC After BCG Failure—Full Text View—ClinicalTrials.gov," ClinicalTrials.gov Identifier: NCT02365818, Retrieved from the Internet: URL:https://clinicaltrials.gov/ct2/show/NCT02365818, last visited Nov. 26, 2020, 8 pages.
Extended European Search Report, dated Feb. 19, 2021, for European Patent Application No. 18784592.0, 8 pages.
Friedlander, T W et al. (May 20, 2012). "Activity of Intravesical CG0070 In Rb-Inactive Superficial Bladder Cancer After BCG Failure: Updated Results of a Phase I/II Trial," Journal of Clinical Oncology 30(15):Abstract No. 4593, 3 pages.
Fukuhara, H. et al. (Oct. 2016, e-pub. Sep. 9, 2016). "Oncolytic virus therapy: A new era of cancer treatment at dawn," Cancer Science 107(10):1373-1379.
GenBank Accession No. AF516106 (Jun. 5, 2002). "*Homo sapiens* E2F Transcription Factor 1 (E2F1) Gene, Complete Cds," 8 pages.
GenBank Accession No. AH006643.2 (Jun. 10, 2016). "*Homo sapiens* Chromosome 20 Transcription Factor E2F1 (E2F1) Gene, Complete Cds," 3 pages.
International Preliminary Report on Patentability, dated Oct. 15, 2019, for PCT Application No. PCT/US2018/02749, filed Apr. 13, 2018, 10 pages.
International Search Report and Written Opinion, dated Jun. 22, 2018, for PCT Application No. PCT/US2018/02749, filed Apr. 13, 2018, 16 pages.
Kaufman, H.L. et al. (Sep. 2015). "Oncolytic Viruses: A New Class Of Immunotherapy Drugs," Nature Reviews. Drug Discovery 14(9):642-662.

(Continued)

*Primary Examiner* — Nicole Kinsey White
(74) *Attorney, Agent, or Firm* — Morrison & Foerster LLP

(57) ABSTRACT

The present invention provides methods for treating an individual having bladder cancer comprising intravesically administering to the individual an oncolytic virus. Also provided are pharmaceutical compositions and kits for treating bladder cancer.

21 Claims, 2 Drawing Sheets

Specification includes a Sequence Listing.

(56) References Cited

OTHER PUBLICATIONS

Lamm, D. et al. (2006), A Phase 1 Dose-Escalation Trial of Intravesical CG0070 for Superficial Transitional Cell Carcinoma (TCC) of the Bladder After Bacillus Calmette-Guerin (BCG) Failure, retrieved from http://media.corporate-ir.net/media_files/IROL/98/98399/V9046_Oncolytic_FINAL_Poster051806.pdf, last visited May 18, 2006, 1 page.

Packiam, V.T. et al. (Oct. 2018, e-pub. Jul. 26, 2017). "An Open Label, Single-Arm, Phase II Multicenter Study Of The Safety and Efficacy Of CG0070 Oncolytic Vector Regimen In Patients With BCG-Unresponsive Non-Muscie-Invasive Bladder Cancer: Interim Results," Urologic Oncology: Seminars and Original Investigations 36(10):440-447.

Packiam, V.T. et al. "Interim Results from A Single-Arm Multicenter Phase II Trial of CG0070, an Oncolytic Adenovirus, for BCG-Unresponsive Non-Muscle-Invasive Bladder Cancer (NMIBC)," retrieved from https://university.auanet.org/abstract_detail.cfm?id=PNFLBA-13&meetingID=17BOS, last visited Apr. 1, 2017.

Ramesh, N et al. (May 2005). "CG0070, A Conditionally Replicating GM-CSF Armed Oncolytic Adenovirus For The Treatment Of Bladder Cancer," Proceedings of the American Association for Cancer Research Annual 46:1185, Abstract: 5019, 4 pages.

Ramesh, N. et al. (Jan. 1, 2006). "CG0070, a Conditionally Replicating Granulocyte Macrophage Colony-Stimulating Factor-Armed Oncolytic Adenovirus for the Treatment of Bladder Cancer," Clin. Cancer Res. 12(1):305-313.

U.S. Appl. No. 17/339,885, filed Jun. 4, 2021, for Yeung et al.

Witjes, J.A. (Feb. 2014). "Bladder Carcinoma In Situ In 2003: State Of The Art," European Urology 45(2):142-146.

\* cited by examiner

METHODS OF TREATING BLADDER CANCER WITH AN ONCOLYTIC VIRUS

CROSS-REFERENCE TO RELATED APPLICATIONS

This application is a U.S. national phase application under 35 U.S.C. § 371 of International Application No. PCT/US2018/027549, filed on Apr. 13, 2018, which claims priority to U.S. Provisional Application No. 62/485,805, filed on Apr. 14, 2017, and U.S. Provisional Application No. 62/500,729, filed on May 3, 2017, all of which are hereby incorporated by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 744442000400SEQLIST.TXT, date recorded: Oct. 8, 2019, size: 3 KB).

FIELD OF THE INVENTION

The present invention relates to methods of treating bladder carcinoma in situ using an oncolytic virus, such as CG0070.

BACKGROUND OF THE INVENTION

Approximately 77,000 new cases of urinary bladder cancer were diagnosed in 2016. Non-muscle invasive bladder cancer (stages Ta, T1, or Carcinoma in situ) accounts for 70-80% of these cases while muscle invasive disease (stage T2 and above) and metastatic disease make up the remaining 20-30%. Bladder cancers are divided into 2 subtypes based on their distinct cellular growth patterns: papillary tumors and flat tumors. Carcinoma in situ is a flat tumor confined to the surface layer of the bladder. Compared to papillary tumors of the Ta and T1 stage, bladder CIS is more difficult to diagnose, and has a high risk of progression to muscle invasive bladder cancer.

Intravesical Bacillus Calmette-Guerin (BCG) is the standard-of-care treatment for bladder CIS. Patients typically receive an induction course consisting of weekly intravesical installations of BCG for 6 weeks, followed by monthly maintenance treatments for 6 to 12 months. However, about 30-40% of patients do not respond to a single course of BCG treatment. In one study, the overall risk of progression among BCG-treated CIS patients with a median follow-up of 2.5 years was about 14%. See, Witjes, J. A. *European urology* 45.2 (2004): 142-146. Since the chance of progression in CIS patients failing BCG is significant, cystectomy, including partial and radical cystectomy, remains the treatment of choice. However, cystectomy is associated with severe side effects and adversely affects patients' quality of life. Moreover, the risk of recurrence after radical cystectomy for clinically localized bladder cancer is high and stage-dependent. See, for example, Bassi P et al. *J. Urol.* 1999; 161:1494-7. The elderly and patients with renal failure, who are less tolerable to surgery or chemotherapy, pose additional clinical challenges for treatment of bladder CIS.

The disclosures of all publications, patents, patent applications and published patent applications referred to herein are hereby incorporated herein by reference in their entirety.

BRIEF SUMMARY OF THE INVENTION

The present application provides methods, compositions (including pharmaceutical compositions) and kits for treating bladder cancer in an individual comprising intravesical administration of an oncolytic virus, e.g., CG0070.

In one aspect, provided herein is a method of treating bladder cancer in an individual, comprising intravesically administering to the individual an effective amount of an oncolytic virus once per week for three weeks during a maintenance phase, wherein the oncolytic virus comprises a viral vector comprising a tumor cell-specific promoter operably linked to a viral gene essential for replication of the oncolytic virus, and a heterologous gene encoding an immune-related molecule.

In another aspect, provided herein is a method of bladder preservation in an individual comprising intravesically administering to the individual an effective amount of an oncolytic virus once per week for three weeks during a maintenance phase, wherein the oncolytic virus comprises a viral vector comprising a tumor cell-specific promoter operably linked to a viral gene essential for replication of the oncolytic virus, and a heterologous gene encoding an immune-related molecule.

In some embodiments, according to any of the methods described above, the oncolytic virus is administered once per week for three weeks every six months during the maintenance phase. In some embodiments, the method further comprises an induction phase prior to the maintenance phase, wherein the induction phase comprises administering to the individual an effective amount of oncolytic virus once per week for six weeks. In some embodiments, the start of the induction phase and the start of the maintenance phase are separated by about 3 months. In some embodiments, the start of the induction phase and the start of the maintenance phase are separated by about 6 months. In some embodiments, the induction phase comprises administering to the individual an effective amount of an oncolytic virus once per week for six weeks on month zero and month three of a treatment regimen.

Also provided herein is a method of treating Ta or T1 bladder cancer in an individual who has not received a transurothelial resection of bladder tumor (TURBT), comprising intravesically administering to the individual an effective amount of an oncolytic virus, wherein the oncolytic virus comprises a viral vector comprising a tumor cell-specific promoter operably linked to a viral gene essential for replication of the oncolytic virus, and a heterologous gene encoding an immune-related molecule.

In one aspect of the present application, there is provided a method of treating bladder cancer in an individual (such as a human), comprising intravesically administering to the individual an effective amount of an oncolytic virus, wherein the oncolytic virus comprises a viral vector comprising a tumor cell-specific promoter operably linked to a viral gene essential for replication of the oncolytic virus, and a heterologous gene encoding an immune-related molecule. In some embodiments, the individual only has bladder carcinoma in situ. In some embodiments, the individual does not have a concurrent papillary carcinoma of Ta or T1 stage. In some embodiments, the individual has bladder carcinoma in situ and a carcinoma of Ta or Ta stage (CIS+Ta or CIS+T1). In some embodiments, the individual has Ta or T1 bladder cancer but not carcinoma in situ. In some embodiments, the individual has Ta or T1 bladder cancer and has not received a transurothelial resection of bladder tumor (TURBT). In some embodiments, the individual has non-resectable Ta or T1 stage bladder cancer. In some embodiments, the individual is unresponsive to BCG treatment. In some embodiments, the individual has disease reoccurrence subsequent to BCG treatment. In some embodiments, the individual has failed the BCG treatment within about 6 months. In some embodiments, the individual is refractory to BCG.

In some embodiments according to any one of the methods described above, the individual has not received a cystectomy. In some embodiments, the individual has refused or is ineligible for a cystectomy. In some embodiments, the cystectomy is radical cystectomy.

In some embodiments according to any one of the methods described above, the oncolytic virus preferentially replicates in a cancer cell. In some embodiments, the cancer cell is defective in the Rb pathway. In some embodiments, the tumor-specific promoter is an E2F-1 promoter. In some embodiments, the E2F-1 promoter comprises the nucleotide sequence set forth in SEQ ID NO:1.

In some embodiments according to any one of the methods described above, the immune-related molecule is selected from the group consisting of GM-CSF, IL-2, IL-12, interferon, CCL4, CCL19, CCL21, CXCL13, TLR1, TLR2, TLR3, TLR4, TLR5, TLR6, TLR7, TLR8, TLR9, TLR10, RIG-I, MDA5, LGP2, and LTαβ. In some embodiments, the immune-related molecule is GM-CSF. In some embodiments, the heterologous gene is operably linked to a viral promoter.

In some embodiments according to any one of the methods described above, the oncolytic virus is selected from the group consisting of adenovirus, herpes simplex virus, vaccinia virus, mumps virus, Newcastle disease virus, polio virus, measles virus, Seneca valley virus, coxsackie virus, reo virus, vesicular stomatitis virus, maraba and rhabdovirus, and parvovirus. In some embodiments, the oncolytic virus is an oncolytic adenovirus. In some embodiments, the viral gene essential for replication of the oncolytic virus is selected from the group consisting of E1A, E1B, and E4. In some embodiments, the heterologous gene is operably linked to an E1 promoter or an E3 promoter. In some embodiments, the oncolytic virus is an adenovirus serotype 5, wherein the endogenous E1a promoter of a native adenovirus is replaced by the human E2F-1 promoter, and the endogenous E3 19 kD coding region of the native adenovirus is replaced by a nucleic acid encoding human GM-CSF. In some embodiments, the oncolytic virus is CG0070.

In some embodiments according to any one of the methods described above, the oncolytic virus is administered at a dose of about $1 \times 10^8$ to about $1 \times 10^{14}$ viral particles.

In some embodiments according to any one of the methods described above, the oncolytic virus is administered weekly. In some embodiments, the oncolytic virus is administered for about 1 week to about 6 weeks.

In some embodiments according to any one of the methods described above, the method further comprises intravesically administering to the individual a transduction enhancing agent prior to the administration of the oncolytic virus. In some embodiments, the transduction enhancing agent is N-Dodecyl-β-D-maltoside (DDM).

In some embodiments according to any one of the methods described above, the method is repeated for at least once.

In some embodiments according to any one of the methods described above, the oncolytic virus is not administered in conjunction with an immune checkpoint modulator.

In some embodiments according to any one of the methods described above, the oncolytic virus is administered as a single therapeutic agent.

Also provided in one aspect is a pharmaceutical composition for treating bladder cancer in an individual (such as a human), wherein the pharmaceutical composition is intravesically administered to the individual, and wherein the pharmaceutical composition comprises an oncolytic virus, wherein the oncolytic virus comprises a viral vector comprising a tumor cell-specific promoter operably linked to a viral gene essential for replication of the oncolytic virus, and a heterologous gene encoding an immune-related molecule.

Further provided in one aspect is use of an oncolytic virus in the preparation of a medicament for treating bladder cancer in an individual (such as a human), wherein the medicament is administered to the individual intravesically, and wherein the oncolytic virus comprises a viral vector comprising a tumor cell-specific promoter operably linked to a viral gene essential for replication of the oncolytic virus, and a heterologous gene encoding an immune-related molecule.

These and other aspects and advantages of the present invention will become apparent from the subsequent detailed description and the appended claims. It is to be understood that one, some, or all of the properties of the various embodiments described herein may be combined to form other embodiments of the present invention.

DETAILED DESCRIPTION OF THE INVENTION

Figure 1:
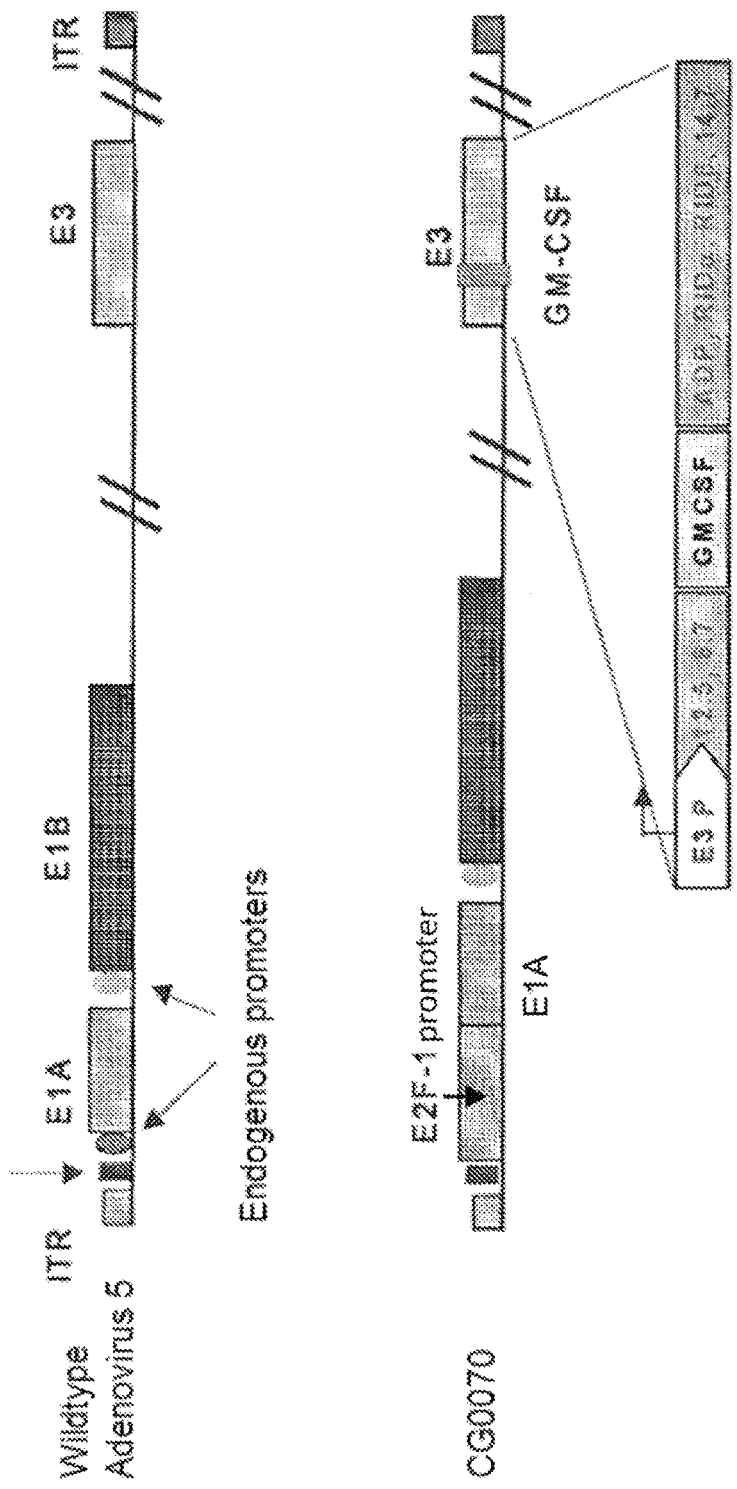
FIG. 1 is a schematic diagram of CG0070 and wild type (wt) adenovirus type 5. CG0070 is based on adenovirus serotype 5, but the endogenous E1a promoter and E3 19 kD coding region have been replaced by the human E2F-1 promoter and a cDNA coding region of human GM-CSF, respectively.

The present invention provides methods and compositions for treating bladder cancer in an individual by intravesically administering to the individual an effective amount of an oncolytic virus, such as CG0070. In vitro studies have suggested that using a conditionally replicating oncolytic virus such as CG0070 could be an effective strategy for treating bladder cancer. Ramesh N, Ge Y, Ennist D L, Zhu M, Mina M, Ganesh S, Reddy P S, Yu D C. CG0070, a conditionally replicating granulocyte macrophage colony-stimulating factor-armed oncolytic adenovirus for the treatment of bladder cancer. Clin Cancer Res. 2006; 12:305-13. However, the unexpected efficacy of CG0070 in certain patient populations and the effect of certain dosing regimens as described herein were previously unknown. The methods are bladder-preserving, highly efficacious and well-tolerated in bladder cancer, including those that have previously failed standard-of-care therapies. In a Phase II clinical trial, inventors surprisingly found that 72.2% of patients with pure CIS, who had previously failed BCG therapy, had complete response (CR) after 6 months of intravesical CG0070 therapy. The therapeutic effects of the oncolytic virus can be achieved using the oncolytic virus as a monotherapeutic agent, or without combination with an immune checkpoint modulator. The methods and compositions described herein are especially useful for patients who have high-risk bladder CIS, but refuse to receive cystectomy, or are ineligible for cystectomy.

Accordingly, one aspect of the present application provides a method of treating bladder cancer in an individual, comprising intravesically administering to the individual an effective amount of an oncolytic virus. In some embodiments, the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus is CG0070. In some embodiments, the oncolytic virus is administered as a single therapeutic agent. In some embodiments, the oncolytic virus is not administered in conjunction with an immune checkpoint modulator. In some embodiments, the individual is not responsive to BCG treatment or has disease reoccurrence subsequent to BCG treatment.

Also provided are compositions (such as pharmaceutical compositions), medicine, kits, and unit dosages useful for the methods described herein.

I. Definitions

Terms are used herein as generally used in the art, unless otherwise defined as follows.

As used herein, "bladder carcinoma in situ," "bladder CIS," and "carcinoma in situ of the bladder" are used interchangeably to refer to the clinical stage of bladder cancer characterized by a flat (i.e., non-papillary) lesion comprising of cytologically malignant cells which may involve either full or partial thickness of the urothelium.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the bladder cancer, diminishing the extent of the bladder cancer, stabilizing the bladder cancer (e.g., preventing or delaying the worsening of the bladder cancer), preventing or delaying the spread (e.g., metastasis) of the bladder cancer, preventing or delaying the recurrence of the bladder cancer, reducing recurrence rate of the bladder cancer, delay or slowing the progression of the bladder cancer, ameliorating the bladder cancer state, providing a remission (partial or total) of the bladder cancer, decreasing the dose of one or more other medications required to treat the bladder cancer, delaying the progression of the bladder cancer, increasing the quality of life, and/or prolonging survival. Also encompassed by "treatment" is a reduction of pathological consequence of bladder cancer. The methods of the invention contemplate any one or more of these aspects of treatment.

"Prior therapy" used herein refers to a therapeutic regime that is different from and was instituted prior to the methods described herein comprising intravesical administration of the oncolytic virus.

As used herein, an "at risk" individual is a human individual who is at risk of developing bladder CIS. A human individual "at risk" may or may not have detectable disease, and may or may not have displayed detectable disease prior to the treatment methods described herein. "At risk" denotes that a human individual has one or more so-called risk factors, which are measurable parameters that correlate with development of muscle invasive bladder cancer, which are described herein. A human individual having one or more of these risk factors has a higher probability of developing bladder CIS than a human individual without these risk factor(s).

"Adjuvant setting" refers to a clinical setting in which an individual has had a history of bladder cancer, and generally (but not necessarily) been responsive to therapy, which includes, but is not limited to, surgery (e.g., transurethral resection of bladder tumor ("TURBT"), partial cystectomy, or radical cystectomy), radiotherapy, and chemotherapy. Treatment or administration in the "adjuvant setting" refers to a subsequent mode of treatment.

"Neoadjuvant setting" refers to a clinical setting in which the method is carried out before the primary/definitive therapy.

The term "individual," "subject," and "patient" are used interchangeably herein to describe a mammal, including humans. An individual includes, but is not limited to, human, bovine, horse, feline, canine, rodent, or primate. In some embodiments, the individual is human. In some embodiments, an individual suffers from bladder CIS. In some embodiments, the individual is in need of treatment.

As used herein, "delaying" the development of bladder cancer means to defer, hinder, slow, retard, stabilise, and/or postpone development of the bladder cancer. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of bladder cancer is a method that reduces probability of disease development in a given time frame and/or reduces the extent of the bladder cancer in a given time frame, when compared to not using the method. Such comparisons are typically based on clinical studies, using a statistically significant number of subjects. Bladder cancer development can be detectable using standard methods, including, but not limited to, urinary cytology, urethra-cystoscopy (UCS), computed tomography (CT Scan, e.g., helical spiral CT scan), endoscopic ultrasound (EUS), endoscopic retrograde cholangiopancreatography (ERCP), laparoscopy, or biopsy (e.g., percutaneous needle biopsy or fine needle aspiration). Development may also refer to bladder cancer progression that may be initially undetectable and includes recurrence.

As used herein, by "combination therapy" is meant that a first agent be administered in conjunction with another agent. "In conjunction with" refers to administration of one treatment modality in addition to another treatment modality. As such, "in conjunction with" refers to administration of one treatment modality before, during, or after delivery of the other treatment modality to the individual.

As used herein, "monotherapy" refers to administration of a single therapeutic agent, such as the oncolytic virus, which is not in conjunction with another treatment modality, such as an immune checkpoint modulator. A monotherapy with the oncolytic virus can be administered with a pretreatment, such as a transduction enhancing agent (e.g., DDM), which is not considered as a different treatment modality for the purpose of this invention.

The term "effective amount" used herein refers to an amount of an agent (such as the oncolytic virus described herein) or composition sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation in cancer. In some embodiments, an effective amount is an amount sufficient to delay development of bladder cancer. In some embodiments, an effective amount is an amount sufficient to prevent or delay recurrence. In some embodiments, an effective amount is an amount sufficient to reduce recurrence rate in the individual. In some embodiments, the effective amount is an amount sufficient to inhibit tumor metastasis in the individual. An effective amount can be administered in one or more administrations. The effective amount of the agent or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent occurrence and/or recurrence of tumor; (vii) delay occurrence and/or recurrence of tumor; (viii) reduce recurrence rate of tumor, and/or (ix) relieve to some extent one or more of the symptoms associated with the cancer. As is understood in the art, an "effective amount" may be in one or more doses, i.e., a single dose or multiple doses may be required to achieve the desired treatment endpoint.

The term "simultaneous administration," as used herein, means that a first therapy and second therapy in a combination therapy are administered at the same time. When the first and second therapies are administered simultaneously, the first and second therapies may be contained in the same composition (e.g., a composition comprising both a first and second therapy) or in separate compositions (e.g., a first therapy is contained in one composition and a second therapy is contained in another composition).

As used herein, the term "sequential administration" or "in sequence" means that the first therapy and second therapy in a combination therapy are administered with a time separation, for example, of more than about 1 minute, such as more than about any of 5, 10, 15, 20, 30, 40, 50, 60, or more minutes. In some cases, the term "sequential administration" means that the first therapy and second therapy in a combination therapy are administered with a time separation of more than about 1 day, such as more than about any of 1 day to 1 week, 2 weeks, 3 weeks, 4 weeks, 8 weeks, 12 weeks, or more weeks. Either the first therapy or the second therapy may be administered first. The first and second therapies are contained in separate compositions, which may be contained in the same or different packages or kits.

The term "administered immediately prior to" means that the first therapy is administered no more than about 15 minutes, such as no more than about any of 10, 5 or 1 minutes before administration of the second therapy. The term "administered immediately after" means that the first therapy is administered no more than about 15 minutes, such as no more than about any of 15, 10 or 1 minutes after administration of the second therapy.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

An "adverse event" or "AE" as used herein refers to any untoward medical occurrence in an individual receiving a marketed pharmaceutical product or in an individual who is participating on a clinical trial who is receiving an investigational or non-investigational pharmaceutical agent. The AE does not necessarily have a causal relationship with the individual's treatment. Therefore, an AE can be any unfavorable and unintended sign, symptom, or disease temporally associated with the use of a medicinal product, whether or not considered to be related to the medicinal product. An AE includes, but is not limited to: an exacerbation of a pre-existing illness; an increase in frequency or intensity of a pre-existing episodic event or condition; a condition detected or diagnosed after study drug administration even though it may have been present prior to the start of the study; and continuously persistent disease or symptoms that were present at baseline and worsen following the start of the study. An AE generally does not include: medical or surgical procedures (e.g., surgery, endoscopy, tooth extraction, or transfusion); however, the condition that leads to the procedure is an adverse event; pre-existing diseases, conditions, or laboratory abnormalities present or detected at the start of the study that do not worsen; hospitalizations or procedures that are done for elective purposes not related to an untoward medical occurrence (e.g., hospitalizations for cosmetic or elective surgery or social/convenience admissions); the disease being studied or signs/symptoms associated with the disease unless more severe than expected for the individual's condition; and overdose of study drug without any clinical signs or symptoms.

A "serious adverse event" or (SAE) as used herein refers to any untoward medical occurrence at any dose including, but not limited to, that: a) is fatal; b) is life-threatening (defined as an immediate risk of death from the event as it occurred); c) results in persistent or significant disability or incapacity; d) requires in-patient hospitalization or prolongs an existing hospitalization (exception: Hospitalization for elective treatment of a pre-existing condition that did not worsen during the study is not considered an adverse event. Complications that occur during hospitalization are AEs and if a complication prolongs hospitalization, then the event is serious); e) is a congenital anomaly/birth defect in the offspring of an individual who received medication; or f) conditions not included in the above definitions that may jeopardize the individual or may require intervention to prevent one of the outcomes listed above unless clearly related to the individual's underlying disease. "Lack of efficacy" (progressive disease) is not considered an AE or SAE. The signs and symptoms or clinical sequelae resulting from lack of efficacy should be reported if they fulfill the AE or SAE definitions.

The following definitions may be used to evaluate response based on target lesions: "complete response" or "CR" refers to disappearance of all target lesions; "partial response" or "PR" refers to at least a 30% decrease in the sum of the longest diameters (SLD) of target lesions, taking as reference the baseline SLD; "stable disease" or "SD" refers to neither sufficient shrinkage of target lesions to qualify for PR, nor sufficient increase to qualify for PD, taking as reference the nadir SLD since the treatment started; and "progressive disease" or "PD" refers to at least a 20% increase in the SLD of target lesions, taking as reference the nadir SLD recorded since the treatment started, or, the presence of one or more new lesions.

The following definitions of response assessments may be used to evaluate a non-target lesion: "complete response" or "CR" refers to disappearance of all non-target lesions; "stable disease" or "SD" refers to the persistence of one or more non-target lesions not qualifying for CR or PD; and "progressive disease" or "PD" refers to the "unequivocal progression" of existing non-target lesion(s) or appearance of one or more new lesion(s) is considered progressive disease (if PD for the individual is to be assessed for a time point based solely on the progression of non-target lesion(s), then additional criteria are required to be fulfilled.

"Progression free survival" (PFS) indicates the length of time during and after treatment that the cancer does not grow. Progression-free survival includes the amount of time individuals have experienced a complete response or a partial response, as well as the amount of time individuals have experienced stable disease.

"Cystectomy free survival" (CFS) indicates the length of time during and after treatment that a cystectomy is not required for the patient as determined by the physician.

"Predicting" or "prediction" is used herein to refer to the likelihood that an individual is likely to respond either favorably or unfavorably to a treatment regimen.

As used herein, "at the time of starting treatment" or "baseline" refers to the time period at or prior to the first exposure to the treatment.

As used herein, "sample" refers to a composition which contains a molecule which is to be characterized and/or identified, for example, based on physical, biochemical, chemical, physiological, and/or genetic characteristics.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Methods of Treating Bladder Cancer

One aspect of the present application relates to treatment of bladder cancer in an individual (such as human individual) by local administration of a virus, such as an oncolytic virus. In this context, local administration of the oncolytic virus encompasses intravesical administration of the oncolytic virus. Any of the methods described herein may be useful for inhibiting growth of a bladder tumor, inhibiting metastasis of a bladder tumor, prolonging survival (such as disease-free survival, progression-free survival, or cystectomy-free survival) of an individual having bladder cancer, causing disease remission in an individual having bladder cancer, preventing disease progression of an individual having bladder cancer, and/or improving quality of life of an individual having bladder cancer. In some embodiments, the method is bladder-preserving or bladder-sparing. In some embodiments, the bladder-preserving or bladder-sparing method is useful for improving the quality of life of the individual.

In some embodiments, provided herein is a method of treating bladder cancer comprising intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule, wherein the oncolytic virus is administered once per week for three weeks. In some embodiments, the oncolytic virus comprises a tumor-selective promoter. In some embodiments, the oncolytic virus is delivered once per week for 6 weeks at month 0 and once per week for 3 weeks at month 6.

In some embodiments, the oncolytic virus is administered during an induction phase and a maintenance phase. In some embodiments, the induction period comprises administering an oncolytic virus once per week for six weeks. In some embodiments, the induction period comprises administering the oncolytic virus once per week for six weeks on months 0 and 3.

In some embodiments, the maintenance phase comprises administering an oncolytic virus once per week for three weeks, following an induction phase. In some embodiments, the maintenance phase comprises delivering the oncolytic virus once per week for three weeks every six months. In some embodiments, the maintenance phase comprises administering the oncolytic virus weekly for three weeks every 6 months 2, 3, 4, 5, 6 times, or as needed. In some embodiments, the maintenance phase comprises administering an oncolytic virus weekly for three weeks on months 6, 12, and 18. In some embodiments, the maintenance phase comprises administering an oncolytic virus weekly for three weeks on months 3, 6, 12, and 18.

In some embodiments, the dosage schedule can be modified based upon the individual's response to the oncolytic virus. For example, in some embodiments, an individual is administered an oncolytic virus once per week for six weeks on month 0 and is reevaluated at month 3. In some embodiments, individuals who have a complete response at month 3 begin a maintenance phase comprising administration of an oncolytic virus once per week for 6 weeks every 6 months. In some embodiments, individuals who do not have a complete response at 3 months receive a second induction dose of oncolytic virus once per week for 6 weeks.

Accordingly, provided herein is a method of treating bladder cancer in an individual comprising administering an oncolytic virus weekly for three weeks every six months, wherein an oncolytic virus (such as CG0070) is administered intervesically, wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the individual is unresponsive or has disease reoccurrence subsequent to BCG treatment. In some embodiments, the individual has refused or is ineligible for cystectomy (such as radical cystectomy). In some embodiments, the method further comprises administering to the individual a transduction enhancing agent (such as DDM) prior to the administration of the oncolytic virus. In some embodiments, the oncolytic virus is administered at a dose of about $1\times10^8$ to about $1\times10^{14}$ viral particles (such as about $1\times10^{12}$ viral particles). In some embodiments, the bladder cancer is CIS, CIS+Ta, CIS+T1, CIS without Ta or T1, Ta, or T1 grade bladder cancer. In some embodiments, the individual has Ta or T1 bladder cancer and has not received a transurothelial resection of bladder tumor (TURBT). In some embodiments, the bladder cancer is Ta or T1 non-resectable bladder cancer. In some embodiments, the oncolytic virus is administered on months 6, 12, and 18 of a treatment regimen. In some embodiments, the oncolytic virus is administered on months 3, 6, 12, and 18 of a treatment regimen. In some embodiments, the oncolytic virus is administered weekly for three weeks, every six months, as needed.

In some embodiments, provided herein is a method of treating bladder cancer comprising administering an oncolytic virus once per week for six weeks during an induction phase and once per week for three weeks during a maintenance phase wherein the an oncolytic virus (such as CG0070) is administered intervesically, wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the individual is unresponsive or has disease reoccurrence subsequent to BCG treatment. In some embodiments, the individual has refused or is ineligible for cystectomy (such as radical cystectomy). In some embodiments, the method further comprises administering to the individual a transduction enhancing agent (such as DDM) prior to the administration of the oncolytic virus. In some embodiments, the oncolytic virus is administered at a dose of about $1\times10^8$ to about $1\times10^{14}$ viral particles (such as about $1\times10^{12}$ viral particles). In some embodiments, the bladder cancer is CIS, CIS+Ta, CIS+T1, CIS without Ta or T1, Ta, or T1 grade bladder cancer. In some embodiments, the bladder cancer is Ta or T1 non-resectable bladder cancer. In some embodiments, the induction phase comprises administering the oncolytic virus once per week for six weeks on months 0 and 3. In some embodiments, the maintenance phase comprises administering the oncolytic virus once per week for three weeks on months 6, 12, and 18. In some embodiments, the maintenance phase comprises administering the oncolytic virus once per week for three weeks on months 3, 6, 12, and 18. In some embodiments, the maintenance phase comprises administering the oncolytic virus once per week for three weeks every six months as needed.

The present methods have the advantage of reducing the need for cystectomy in patients and thus may be used in bladder sparing methods and to treat patients who are ineligible for or refuse cystectomy. Accordingly, in some embodiments, provided herein is bladder sparing method comprising in an individual comprising administering an oncolytic virus weekly for three weeks every six months, wherein an oncolytic virus (such as CG0070) is administered intervesically, wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the individual is unresponsive or has disease reoccurrence subsequent to BCG treatment. In some embodiments, the individual has refused or is ineligible for cystectomy (such as radical cystectomy). In some embodiments, the method further comprises administering to the individual a transduction enhancing agent (such as DDM) prior to the administration of the oncolytic virus. In some embodiments, the oncolytic virus is administered at a dose of about $1\times10^8$ to about $1\times10^{14}$ viral particles (such as about $1\times10^{12}$ viral particles). In some embodiments, the bladder cancer is CIS, CIS+Ta, CIS+T1, CIS without Ta or T1, Ta, or T1 grade bladder cancer. In some embodiments, the individual has Ta or T1 bladder cancer and has not received a transurothelial resection of bladder tumor (TURBT). In some embodiments, the bladder cancer is Ta or T1 non-resectable bladder cancer. In some embodiments, the oncolytic virus is administered on months 6, 12, and 18 of a treatment regimen. In some embodiments, the oncolytic virus is administered on months 3, 6, 12, and 18 of a treatment regimen. In some embodiments, the oncolytic virus is administered weekly for three weeks, every six months, as needed.

In some embodiments, provided herein is a method of maintenance therapy comprising administering an oncolytic virus weekly for three weeks every six months, wherein an oncolytic virus (such as CG0070) is administered intervesically, wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the individual is unresponsive or has disease reoccurrence subsequent to BCG treatment. In some embodiments, the individual has refused or is ineligible for cystectomy (such as radical cystectomy). In some embodiments, the method further comprises administering to the individual a transduction enhancing agent (such as DDM) prior to the administration of the oncolytic virus. In some embodiments, the oncolytic virus is administered at a dose of about $1\times10^8$ to about $1\times10^{14}$ viral particles (such as about $1\times10^{12}$ viral particles). In some embodiments, the bladder cancer is CIS, CIS+Ta, CIS+T1, CIS without Ta or T1, Ta, or T1 grade bladder cancer. In some embodiments, the individual has Ta or T1 bladder cancer and has not received a transurothelial resection of bladder tumor (TURBT). In some embodiments, the bladder cancer is Ta or T1 non-resectable bladder cancer. In some embodiments, the oncolytic virus is administered on months 6, 12, and 18 of a treatment regimen. In some embodiments, the oncolytic virus is administered on months 3, 6, 12, and 18 of a treatment regimen. In some embodiments, the oncolytic virus is administered weekly for three weeks, every six months, as needed.

In some embodiments, the individual receives no more than 21 doses of an oncolytic virus. In some embodiments, the individual receives no more than 30, 25, 20, 15, 14, 13, 12, 11, 10, 9, 8, 7, or 6 doses of an oncolytic virus.

In some embodiments, there is provided a method of treating bladder cancer (such as CIS bladder cancer or Ta or T1 grade bladder cancer without TURBT) in an individual, comprising intravesically administering to the individual an effective amount of an oncolytic virus (such as oncolytic adenovirus) comprising a viral vector comprising a tumor cell-specific promoter operably linked to a viral gene essential for replication of the oncolytic virus. In some embodiments, the oncolytic virus comprises a tumor-selective promoter. In some embodiments, the tumor selective promoter allows preferential replication of the oncolytic virus in tumor cells. In some embodiments, the oncolytic virus preferentially replicates in a cancer cell, such as a cancer cell defective in the Rb pathway. In some embodiments, the oncolytic virus is selected from the group consisting of adenovirus, herpes simplex virus, vaccinia virus, mumps virus, Newcastle disease virus, polio virus, measles virus, Seneca valley virus, coxsackie virus, reo virus, vesicular stomatitis virus, maraba and rhabdovirus, and parvovirus. In some embodiments, the tumor-specific promoter is an E2F-1 promoter, such as a human E2F-1 promoter or an E2F-1 promoter comprising the nucleotide sequence set forth in SEQ ID NO:1. In some embodiments, the viral gene essential for replication of the oncolytic virus is selected from the group consisting of E1A, E1B, and E4.

In some embodiments, the oncolytic virus further comprises an immune-related molecule (such as cytokine, chemokine, or PRRago (i.e., pathogen recognition receptor agonist)). In some embodiments, the immune-related molecule is not an immune checkpoint modulator. In some embodiments, the immune-related molecule is selected from the group consisting of GM-CSF, IL-2, IL-12, interferon (such as Type 1, Type 2 or Type 3 interferon, e.g., interferon γ), CCL4, CCL19, CCL21, CXCL13, TLR1, TLR2, TLR3, TLR4, TLR5, TLR6, TLR7, TLR8, TLR9, TLR10, RIG-I, MDA5, LGP2, and LTαβ. In some embodiments, the immune-related molecule is selected from the group consisting of STING (i.e., stimulator of interferon genes) activators (such as CDN, i.e., cyclic dinucleotides), PRRago (such as CpG, Imiquimod, or Poly I:C), TLR stimulators (such as GS-9620, AED-1419, CYT-003-QbG10, AVE-0675, or PF-7909), and RLR stimulators (such as RIG-I, Mda5, or LGP2 stimulators). In some embodiments, the immune-related molecule induces dendritic cells, T cells, B cells, and/or T follicular helper cells.

In some embodiments, the immune-related molecule is expressed by the oncolytic virus. For example, the oncolytic virus may comprise a nucleic acid encoding the immune-related molecule, and the nucleic acid can be in the viral vector or on a separate vector. In some embodiments, the oncolytic virus is a virus comprising a viral vector, and wherein the viral vector comprises the nucleic acid encoding the immune-related molecule. In some embodiments, the nucleic acid encoding the immune-related molecule is operably linked to a viral promoter, such as an E1 promoter, or an E3 promoter.

In some embodiments, the immune-related molecule enhances an immune response in the individual. Immune-related molecules may include, but are not limited to, a cytokine, a chemokine, a stem cell growth factor, a lymphotoxin, an hematopoietic factor, a colony stimulating factor (CSF), erythropoietin, thrombopoietin, tumor necrosis factor-alpha (TNF), TNF-beta, granulocyte-colony stimulating factor (G-CSF), granulocyte macrophage-colony stimulating factor (GM-CSF), interferon-alpha, interferon-beta, interferon-gamma, interferon-lambda, stem cell growth factor designated "S1 factor", human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, mullerian-inhibiting substance, mouse gonadotropin-associated peptide, inhibin, activin, vascular endothelial growth factor, integrin, NGF-beta, platelet-growth factor, TGF-alpha, TGF-beta, insulin-like growth factor-I, insulin-like growth factor-II, macrophage-CSF (M-CSF), IL-1, IL-1a, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin, lymphotoxin, thalidomide, lenalidomide, or pomalidomide.

Thus, in some embodiments, there is provided a method of treating bladder cancer (such as CIS bladder cancer or Ta or T1 grade bladder cancer without TURBT) in an individual, comprising intravesically administering to the individual an effective amount of an oncolytic virus, wherein the oncolytic virus comprises a viral vector comprising a tumor cell-specific promoter operably linked to a viral gene essential for replication of the oncolytic virus and a nucleic acid encoding an immune-related molecule (such as cytokine or chemokine) operably linked to a viral promoter. In some embodiments, the oncolytic virus comprises a tumor-selective promoter. In some embodiments, the tumor-specific promoter is an E2F-1 promoter, such as a human E2F-1 promoter or an E2F-1 promoter comprising the nucleotide sequence set forth in SEQ ID NO:1. In some embodiments, the viral gene essential for replication of the oncolytic virus is selected from the group consisting of E1A, E1B, and E4. In some embodiments, the viral promoter operably linked to the nucleic acid encoding the immune-related molecule is the E3 promoter. In some embodiments, the immune-related molecule is GM-CSF. In some embodiments, the method further comprises administering to the individual a transduction enhancing agent (such as DDM) prior to the administration of the oncolytic virus. In some embodiments, the oncolytic virus is administered at a dose of about $1\times10^8$ to about $1\times10^{14}$ viral particles (such as about $1\times10^{12}$ viral particles). In some embodiments, the oncolytic virus is administered weekly. In some embodiments, the oncolytic virus is administered for about 1 week to about 6 weeks (such as about 6 weeks or about 3 weeks). In some embodiments, the bladder cancer is CIS, CIS+Ta, CIS+T1, Ta, or T1 grade bladder cancer.

In some embodiments, the oncolytic virus is an adenovirus serotype 5. In some embodiments, the endogenous E1a promoter and E3 19 kD coding region of a native adenovirus is replaced by the human E2F-1 promoter and a nucleic acid encoding human GM-CSF. In some embodiments, a polyadenylation signal (PA) is inserted 5' of the E2F-1 promoter. In some embodiments, the nucleic acid encoding human GM-CSF is operably linked to the E3 promoter. In some embodiments, the vector backbone of the adenovirus serotype 5 further comprises E2, E4, late protein regions or inverted terminal repeats (ITRs) identical to the wildtype adenovirus serotype 5 genome. In some embodiments, the oncolytic virus has the genomic structure as shown in FIG. 1. In some embodiments, the oncolytic virus is conditionally replicating. In some embodiments, the oncolytic virus preferentially replicates in cancer cells. In some embodiments, the cancer cells are Rb pathway-defective cancer cells. In some embodiments, the oncolytic virus is CG0070.

Thus, in some embodiments, there is provided a method of treating bladder cancer (such as CIS bladder cancer or Ta or T1 grade bladder cancer without TURBT) in an individual, comprising intravesically administering to the individual an effective amount of an adenovirus serotype 5, wherein the endogenous E1a promoter and E3 19 kD coding region of a native adenovirus is replaced by the human E2F-1 promoter and a nucleic acid encoding an immune-related molecule (such as cytokine or chemokine, for example, GM-CSF). In some embodiments, the tumor-specific promoter is a human E2F-1 promoter or an E2F-1 promoter comprising the nucleotide sequence set forth in SEQ ID NO:1. In some embodiments, the method further comprises administering to the individual a transduction enhancing agent (such as DDM) prior to the administration of the adenovirus. In some embodiments, the adenovirus is administered at a dose of about $1\times10^8$ to about $1\times10^{14}$ viral particles (such as about $1\times10^{12}$ viral particles). In some embodiments, the adenovirus is administered weekly. In some embodiments, the adenovirus is administered for about 1 week to about 6 weeks (such as about 6 weeks or about 3 weeks). In some embodiments, the bladder cancer is CIS, CIS+Ta, CIS+T1, Ta, or T1 grade bladder cancer.

In some embodiments, there is provided a method of treating bladder cancer (such as CIS bladder cancer or Ta or T1 grade bladder cancer without TURBT), comprising intravesically administering to the individual an effective amount of CG0070. In some embodiments, the method further comprises administering to the individual a transduction enhancing agent (such as DDM) prior to the administration of CG0070. In some embodiments, CG0070 is administered at a dose of about $1\times10^8$ to about $1\times10^{14}$ viral particles (such as about $1\times10^{12}$ viral particles). In some embodiments, CG0070 is administered weekly. In some embodiments, CG0070 is administered for about 1 week to about 6 weeks (such as about 6 weeks or about 3 weeks). In some embodiments, the bladder cancer is CIS, CIS+Ta, CIS+T1, Ta, or T1 grade bladder cancer.

In some embodiments, the oncolytic virus is not administered to the individual in conjunction with an immune checkpoint modulator. In some embodiments, the oncolytic virus is administered to the individual as a single therapeutic agent. As used herein, "immune checkpoint modulator" refers to a molecule or an agent (such as antibody) that inhibits an inhibitory immune checkpoint molecule or an immune-stimulating agent that activates an immune stimulatory molecule on an immune cell (such as T cell) or a tumor cell. "Immune checkpoint molecules" include molecules that turn up an immune signal (i.e., "immune stimulatory molecules"), or molecules that turn down an immune signal (i.e., "inhibitory immune checkpoint molecules") against a tumor cell.

In some embodiments, the oncolytic virus is not administered to the individual in conjunction with an immune-stimulating agent. The immune-stimulating agent may be a natural or engineered ligand of an immune stimulatory molecule selected from the group consisting of ligands of OX40 (e.g., OX40L), ligands of CD-28 (e.g., CD80, CD86), ligands of ICOS (e.g., B7RP1), ligands of 4-1BB (e.g., 4-1BBL, Ultra4-1BBL), ligands of CD27 (e.g., CD70), ligands of CD40 (e.g., CD40L), and ligands of TCR (e.g., MEW class I or class II molecules, IMCgp100). The immune-stimulating agent may also be an antibody selected from the group consisting of anti-CD28 (e.g., TGN-1412), anti-OX40 (e.g., MEDI6469, MEDI-0562), anti-ICOS (e.g., MEDI-570), anti-GITR (e.g., TRX518, INBRX-110, NOV-120301), anti-41-BB (e.g., BMS-663513, PF-05082566), anti-CD27 (e.g., BION-1402, Varlilumab and hCD27.15), anti-CD40 (e.g., CP870,893, BI-655064, BMS-986090, APX005, APX005M), anti-CD3 (e.g., blinatumomab, muromonab), and anti-HVEM.

In some embodiments, the oncolytic virus is not administered to the individual in conjunction with an immune checkpoint inhibitor. The immune-checkpoint inhibitor may be a natural or engineered ligand of an inhibitory immune checkpoint molecule selected from the group consisting of ligands of CTLA-4 (e.g., B7.1, B7.2), ligands of TIM3 (e.g., Galectin-9), ligands of A2a Receptor (e.g., adenosine, Regadenoson), ligands of LAG3 (e.g., MHC class I or MHC class II molecules), ligands of BTLA (e.g., HVEM, B7-H4), ligands of KIR (e.g., MHC class I or MHC class II molecules), ligands of PD-1 (e.g., PD-L1, PD-L2), ligands of IDO (e.g., NKTR-218, Indoximod, NLG919), and ligands of CD47 (e.g., SIRP-alpha receptor). The immune checkpoint inhibitor may also be an antibody that targets an inhibitory immune checkpoint protein selected from the group consisting of anti-CTLA-4 (e.g., Ipilimumab, Tremelimumab, KAHR-102), anti-TIM3 (e.g., F38-2E2, ENUM005), anti-LAG3 (e.g., BMS-986016, IMP701, IMP321, C9B7W), anti-KIR (e.g., Lirilumab and IPH2101), anti-PD-1 (e.g., Nivolumab, Pidilizumab, Pembrolizumab, BMS-936559, atezolizumab, Lambrolizumab, MK-3475, AMP-224, AMP-514, STI-A1110, TSR-042), anti-PD-L1 (e.g., KY-1003 (EP20120194977), MCLA-145, RG7446, BMS-936559, MEDI-4736, MSB0010718C, AUR-012, STI-A1010, PCT/US2001/020964, MPDL3280A, AMP-224, Dapirolizumab pegol (CDP-7657), MEDI-4920), anti-CD73 (e.g., AR-42 (OSU-HDAC42, HDAC-42, AR42, AR 42, OSU-HDAC 42, OSU-HDAC-42, NSC D736012, HDAC-42, HDAC 42, HDAC42, NSCD736012, NSC-D736012), MEDI-9447), anti-B7-H3 (e.g., MGA271, DS-5573a, 8H9), anti-CD47 (e.g., CC-90002, TTI-621, VLST-007), anti-BTLA, anti-VISTA, anti-A2aR, anti-B7-1, anti-B7-H4, anti-CD52 (such as alemtuzumab), anti-IL-10, anti-IL-35, and anti-TGF-β (such as Fresolumimab).

Thus, in some embodiments, there is provided a method of treating bladder cancer (such as CIS bladder cancer or Ta or T1 grade bladder cancer without TURBT) in an individual, comprising intravesically administering to the individual an effective amount of an oncolytic virus (such as oncolytic adenovirus) comprising a viral vector comprising a tumor cell-specific promoter operably linked to a viral gene essential for replication of the oncolytic virus and a nucleic acid encoding an immune-related molecule (such as cytokine or chemokine) operably linked to a viral promoter, wherein the oncolytic virus is administered as a single therapeutic agent. In some embodiments, the oncolytic virus comprises a tumor-selective promoter. In some embodiments, there is provided a method of treating bladder cancer in an individual, comprising intravesically administering to the individual an effective amount of an oncolytic virus (such as oncolytic adenovirus) comprising a viral vector comprising a tumor cell-specific promoter operably linked to a viral gene essential for replication of the oncolytic virus and a nucleic acid encoding an immune-related molecule (such as cytokine or chemokine) operably linked to a viral promoter, wherein the oncolytic virus is not administered in conjunction with an immune checkpoint modulator. In some embodiments, the tumor-specific promoter is an E2F-1 promoter, such as a human E2F-1 promoter or an E2F-1 promoter comprising the nucleotide sequence set forth in SEQ ID NO:1. In some embodiments, the viral gene essential for replication of the oncolytic virus is selected from the group consisting of E1A, E1B, and E4. In some embodiments, the viral promoter operably linked to the nucleic acid encoding the immune-related molecule is the E3 promoter. In some embodiments, the immune-related molecule is GM-CSF. In some embodiments, the method further comprises administering to the individual a transduction enhancing agent (such as DDM) prior to the administration of the oncolytic virus. In some embodiments, the oncolytic virus is administered at a dose of about $1\times10^8$ to about $1\times10^{14}$ viral particles (such as about $1\times10^{12}$ viral particles). In some embodiments, the oncolytic virus is administered weekly. In some embodiments, the oncolytic virus is administered for about 1 week to about 6 weeks (such as about 6 weeks or about 3 weeks). In some embodiments, the bladder cancer is CIS, CIS+Ta, CIS+T1, Ta, or T1 grade bladder cancer.

In some embodiments, there is provided a method of treating bladder cancer (such as CIS bladder cancer or Ta or T1 grade bladder cancer without TURBT) in an individual, comprising intravesically administering to the individual an effective amount of an adenovirus serotype 5, wherein the endogenous E1a promoter and E3 19 kD coding region of a native adenovirus is replaced by the human E2F-1 promoter and a nucleic acid encoding an immune-related molecule (such as cytokine or chemokine, for example, GM-CSF), wherein the adenovirus is administered as a single therapeutic agent. In some embodiments, there is provided a method of treating bladder carcinoma in situ in an individual, comprising intravesically administering to the individual an effective amount of an adenovirus serotype 5, wherein the endogenous E1a promoter and E3 19 kD coding region of a native adenovirus is replaced by the human E2F-1 promoter and a nucleic acid encoding an immune-related molecule (such as cytokine or chemokine, for example, GM-CSF), wherein the adenovirus is not administered in conjunction with an immune checkpoint modulator. In some embodiments, the tumor-specific promoter is a human E2F-1 promoter or an E2F-1 promoter comprising the nucleotide sequence set forth in SEQ ID NO:1. In some embodiments, the method further comprises administering to the individual a transduction enhancing agent (such as DDM) prior to the administration of the adenovirus. In some embodiments, the adenovirus is administered at a dose of about $1\times10^8$ to about $1\times10^{14}$ viral particles (such as about $1\times10^{12}$ viral particles). In some embodiments, the adenovirus is administered weekly. In some embodiments, the adenovirus is administered for about 1 week to about 6 weeks (such as about 3 weeks or about 6 weeks). In some embodiments, the bladder cancer is CIS, CIS+Ta, CIS+T1, Ta, or T1 grade bladder cancer.

In some embodiments, there is provided a method of treating bladder cancer (such as CIS bladder cancer or Ta or T1 grade bladder cancer without TURBT) in an individual, comprising intravesically administering to the individual an effective amount of CG0070, wherein CG0070 is administered as a single therapeutic agent. In some embodiments, there is provided a method of treating bladder carcinoma in situ in an individual, comprising intravesically administering to the individual an effective amount of CG0070, wherein CG0070 is not administered in conjunction with an immune checkpoint modulator. In some embodiments, the method further comprises administering to the individual a transduction enhancing agent (such as DDM) prior to the administration of CG0070. In some embodiments, CG0070 is administered at a dose of about $1\times10^8$ to about $1\times10^{14}$ viral particles (such as about $1\times10^{12}$ viral particles). In some embodiments, CG0070 is administered weekly. In some embodiments, CG0070 is administered for about 1 week to about 6 weeks (such as about 3 weeks or about 6 weeks). In some embodiments, the bladder cancer is CIS, CIS+Ta, CIS+T1, Ta, or T1 grade bladder cancer.

Patient Populations

The methods described herein can be used to treat a variety of bladder cancers. In some embodiments, the individual has a bladder cancer at a stage Ta, T1, or CIS (TIS) as determined according to the TNM staging system by the American Joint Committee on Cancer (AJCC) guidelines.

In some embodiments the bladder cancer is CIS. In some embodiments, the bladder CIS is transitional cell carcinoma or urothelial carcinoma. In some embodiments, the bladder CIS is metastatic urothelial carcinoma. In some embodiments, the bladder CIS is located in the urothelium of the bladder. In some embodiments, the bladder CIS is located in the upper urinary tract. In some embodiments, the bladder CIS is in the ureter. In some embodiments, the bladder CIS is in the urethra. In some embodiments, the bladder CIS is in the renal pelvis.

"Bladder carcinoma in situ" is a high-grade bladder cancer, also known as Stage 0 is, Tis, flat, or bladder CIS. Bladder CIS is found only on the inner lining of the bladder, and it has not grown in toward the hollow part of the bladder, and it has not spread to the thick layer of muscle or connective tissue of the bladder. Bladder CIS is considered an aggressive disease, and believed to be a precursor of invasive bladder cancer. According to NCCN Guidelines for Bladder Cancer, current standard therapy for bladder CIS is resection followed by intravesical therapy with BCG. BCG is generally given once a week for 6 weeks, followed by a rest period of 4 to 6 weeks, with a full re-evaluation at week 12 after the start of therapy. If the patient is unable to tolerate BCG, intravesical mitomycin C may be administered.

In some embodiments, the individual has a pathological stage of "pure CIS" or "CIS," wherein the individual has one or more bladder carcinomas in situ only. In some embodiments, the individual has a pathological stage of Tis, N0, M0. In some embodiments, the bladder CIS is a primary tumor. In some embodiments, the bladder CIS is a recurrent tumor. In some embodiments, the individual has at least about any one of 1, 2, 3, 4, 5, 10, or more bladder carcinomas in situ.

In some embodiments, the individual has concurrently one or more bladder carcinomas in situ and one or more papillary carcinomas of Ta or T1 stage. In some embodiments, the individual has a pathological stage of "CIS+Ta," wherein the individual has concurrently one or more bladder carcinomas in situ and one or more Ta stage papillary carcinomas. In some embodiments, the individual has a pathological stage of "CIS+T1," wherein the individual has concurrently one or more bladder carcinomas in situ and one or more T1 stage papillary carcinomas.

"Papillary carcinoma" refers to bladder tumors that grow in slender, finger-like projections from the inner surface of the bladder toward the hollow center. Papillary tumors often grow toward the center of the bladder without growing into the deeper bladder layers. These tumors are called non-invasive papillary cancers. Very low-grade (slow growing), non-invasive papillary cancer is sometimes called papillary urothelial neoplasm of low-malignant potential (PUNLMP).

"Ta" stage papillary carcinoma refers to papillary carcinoma that is found on the surface of the inner lining of the bladder. Cancer cells are grouped together and can often be easily removed. The cancer has not invaded the muscle or connective tissue of the bladder wall. Ta papillary carcinoma is also referred to as noninvasive papillary urothelial carcinoma, or Stage 0a bladder cancer.

"T1" stage papillary carcinoma refers to papillary carcinoma that has grown through the inner lining of the bladder into the lamina propria. It has not spread to the thick layer of muscle in the bladder wall or to lymph nodes or other organs. In some embodiments, the carcinoma has invaded subepithelial connective tissue.

In some embodiments, the individual does not have a concurrent papillary carcinoma with CIS. In some embodiments, the individual does not have low-grade or high-grade papillary carcinoma. In some embodiments, the individual does not have high-grade papillary carcinoma. In some embodiments, the individual does not have a concurrent papillary carcinoma of low-grade Ta stage. In some embodiments, the individual does not have a concurrent papillary carcinoma of high-grade Ta stage. In some embodiments, the individual does not have a concurrent papillary carcinoma of low-grade T1 stage. In some embodiments, the individual does not have a concurrent papillary carcinoma of high-grade T1 stage. In some embodiments, the individual does not have a concurrent papillary carcinoma of Ta or T1 stage.

In some embodiments, the individual has a papillary carcinoma. In some embodiments, the individual has a low-grade or high-grade papillary carcinoma concurrent with CIS. In some embodiments, the individual has a high-grade papillary carcinoma. In some embodiments, the individual has a concurrent papillary carcinoma of low-grade Ta stage. In some embodiments, the individual has a concurrent papillary carcinoma of high-grade Ta stage. In some embodiments, the individual does not have a concurrent papillary carcinoma of low-grade T1 stage. In some embodiments, the individual does not have a concurrent papillary carcinoma of high-grade T1 stage. In some embodiments, the individual does not have a concurrent papillary carcinoma of Ta or T1 stage.

In some embodiments, the individual has a papillary carcinoma without CIS. In some embodiments, the individual has a low-grade or high-grade papillary carcinoma. In some embodiments, the individual has a high-grade papillary carcinoma. In some embodiments, the individual has a concurrent papillary carcinoma of low-grade Ta stage. In some embodiments, the individual has a concurrent papillary carcinoma of high-grade Ta stage. In some embodiments, the individual does not have a concurrent papillary carcinoma of low-grade T1 stage. In some embodiments, the individual does not have a concurrent papillary carcinoma of high-grade T1 stage. In some embodiments, the individual has Ta or T1 stage bladder cancer without CIS.

Bladder cancer can be detected and staged using any known methods in the art, including, but not limited to, urinary cytology, urethra-cystoscopy (UCS), biopsy (such as transurethral resection of bladder tumor, or "TURBT"), computed tomography (CT or CAT) scan (e.g., CT urography), magnetic resonance imaging (MRI, i.e., MR urography), positron emission tomography (PET or PET-CT) scan, ultrasound (e.g., renal ultrasound), ureteroscopy, and x-ray imaging (e.g., chest imaging). A distinct feature of bladder CIS is the fact that coherence and adherence of CIS cells are decreased. As a result, more cells are present in urine, which can be detected by urinary cytology. Additionally, bladder CIS is associated with an increased chance of denuded epithelium upon biopsy. Tumor cells from urinary samples or biopsy samples can be examined using immunohistochemistry, ELISA, RT-PCR, or other suitable methods to detect urinary markers for bladder CIS or papillary tumors. Fluorescence cystoscopy methods, e.g., those using a porphyrin-based phososensitizer, may be especially suitable for detecting CIS lesions.

Thus, in some embodiments, there is provided a method of treating an individual having bladder carcinoma in situ only, comprising intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the method further comprises administering to the individual a transduction enhancing agent (such as DDM) prior to the administration of the oncolytic virus. In some embodiments, the oncolytic virus is administered at a dose of about $1\times10^8$ to about $1\times10^{14}$ viral particles (such as about $1\times10^{12}$ viral particles). In some embodiments, the oncolytic virus is administered weekly. In some embodiments, the oncolytic virus is administered for about 1 week to about 6 weeks (such as about 3 weeks or about 6 weeks).

In some embodiments, there is provided a method of treating an individual having bladder CIS, comprising intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule, and wherein the individual does not have a concurrent papillary carcinoma of Ta or T1 stage. In some embodiments, the oncolytic virus is not administered in conjunction with an immune checkpoint modulator. In some embodiments, the oncolytic virus is administered as a single therapeutic agent. In some embodiments, the method further comprises administering to the individual a transduction enhancing agent (such as DDM) prior to the administration of the oncolytic virus. In some embodiments, the oncolytic virus is administered at a dose of about $1\times10^8$ to about $1\times10^{14}$ viral particles (such as about $1\times10^{12}$ viral particles). In some embodiments, the oncolytic virus is administered weekly. In some embodiments, the oncolytic virus is administered for about 1 week to about 6 weeks (such as about 3 weeks or about 6 weeks).

In some embodiments, there is provided a method of treating an individual having bladder CIS (such as pure CIS), comprising intravesically administering to the individual CG0070, wherein CG0070 is administered weekly at a dose of about $1\times10^8$ to about $1\times10^{14}$ viral particles (such as about $1\times10^{12}$ viral particles) for about 3 or about 6 weeks. In some embodiments, the method further comprises administering to the individual a transduction enhancing agent (such as DDM) prior to the administration of CG0070. In some embodiments, CG0070 is not administered in conjunction with an immune checkpoint modulator. In some embodiments, CG0070 is administered as a single therapeutic agent. In some embodiments, the individual is unresponsive or has disease reoccurrence subsequent to BCG treatment. In some embodiments, the individual has refused or is ineligible for cystectomy (such as radical cystectomy).

In some embodiments, there is provided a method of treating an individual having T1 stage bladder cancer with CIS, comprising intravesically administering to the individual CG0070, wherein CG0070 is administered weekly at a dose of about $1\times10^8$ to about $1\times10^{14}$ viral particles (such as about $1\times10^{12}$ viral particles) for about 3 or about 6 weeks. In some embodiments, the method further comprises administering to the individual a transduction enhancing agent (such as DDM) prior to the administration of CG0070. In some embodiments, CG0070 is not administered in conjunction with an immune checkpoint modulator. In some embodiments, CG0070 is administered as a single therapeutic agent. In some embodiments, the individual is unresponsive or has disease reoccurrence subsequent to BCG treatment. In some embodiments, the individual has refused or is ineligible for cystectomy (such as radical cystectomy).

In some embodiments, there is provided a method of treating an individual having Ta stage bladder cancer with CIS, comprising intravesically administering to the individual CG0070, wherein CG0070 is administered weekly at a dose of about $1\times10^8$ to about $1\times10^{14}$ viral particles (such as about $1\times10^{12}$ viral particles) for about 6 weeks. In some embodiments, the method further comprises administering to the individual a transduction enhancing agent (such as DDM) prior to the administration of CG0070. In some embodiments, CG0070 is not administered in conjunction with an immune checkpoint modulator. In some embodiments, CG0070 is administered as a single therapeutic agent. In some embodiments, the individual is unresponsive or has disease reoccurrence subsequent to BCG treatment. In some embodiments, the individual has refused or is ineligible for cystectomy (such as radical cystectomy).

In some embodiments, there is provided a method of treating an individual having T1 stage bladder cancer without CIS, comprising intravesically administering to the individual CG0070, wherein CG0070 is administered weekly at a dose of about $1\times10^8$ to about $1\times10^{14}$ viral particles (such as about $1\times10^{12}$ viral particles) for about 6 weeks. In some embodiments, the method further comprises administering to the individual a transduction enhancing agent (such as DDM) prior to the administration of CG0070. In some embodiments, CG0070 is not administered in conjunction with an immune checkpoint modulator. In some embodiments, CG0070 is administered as a single therapeutic agent. In some embodiments, the individual is unresponsive or has disease reoccurrence subsequent to BCG treatment. In some embodiments, the individual has refused or is ineligible for cystectomy (such as radical cystectomy).

In some embodiments, there is provided a method of treating an individual having Ta stage bladder cancer without CIS, comprising intravesically administering to the individual CG0070, wherein CG0070 is administered weekly at a dose of about $1\times10^8$ to about $1\times10^{14}$ viral particles (such as about $1\times10^{12}$ viral particles) for about 6 weeks. In some embodiments, the method further comprises administering to the individual a transduction enhancing agent (such as DDM) prior to the administration of CG0070. In some embodiments, CG0070 is not administered in conjunction with an immune checkpoint modulator. In some embodiments, CG0070 is administered as a single therapeutic agent. In some embodiments, the individual is unresponsive or has disease reoccurrence subsequent to BCG treatment. In some embodiments, the individual has refused or is ineligible for cystectomy (such as radical cystectomy).

In some embodiments, the individual has early stage bladder cancer, non-metastatic bladder cancer, non-invasive bladder cancer, non-muscle-invasive bladder cancer, primary bladder cancer, locally advanced bladder cancer (such as unresectable locally advanced bladder cancer), metastatic bladder cancer, or bladder cancer in remission. In some embodiments, the bladder cancer is localized resectable, localized unresectable, or unresectable. In some embodiments, the bladder cancer is a high grade, non-muscle-invasive cancer that has been refractory to standard intra-bladder infusion (intravesical) therapy. In some embodiments, the individual has a high grade, non-muscle-invasive CIS that has been refractory to standard intra-bladder infusion (intravesical) therapy. In some embodiments, the individual has urothelial (i.e., transitional cell) carcinoma.

The methods provided herein can be used to treat an individual (e.g., human) who has been diagnosed with or is suspected of having bladder cancer. In some embodiments, the individual has undergone a tumor resection, such as TURBT, or partial cystectomy. In some embodiments, the individual has previously received TURBT alone. In some embodiments, the individual has previously received TURBT and concurrent chemoradiotherapy. In some embodiments, the individual has previously received repeated TURBT. In some embodiments, the individual has previously received TURBT for at least about any one of 1, 2, 3, 4, or more times. In some embodiments, the individual has previously received maximal TURBT. In some embodiments, the individual has not received a tumor resection. According to the NCCN Guidelines for Bladder Cancer, bladder preservation with maximal TURBT and concurrent chemoradiotherapy is generally reserved for patients with smaller solitary tumors, negative nodes, no carcinoma in situ, no tumor-related hydronephrosis, and good pre-treatment bladder function.

In some embodiments, the methods provided herein can be used to treat an individual with bladder cancer who has not received a TURBT, or partial cystectomy prior to treatment with CG0070. In some embodiments, the individual has a Ta or T1 stage cancer. In some embodiments, the individual is considered unresectable or with residual disease. In some embodiments, the individual has an underlying medical condition that does not permit adequate resection.

Accordingly, in some embodiments, there is provided a method of treating an individual having T1 or Ta stage bladder cancer that is has not been resected or is considered non-resectable, comprising intravesically administering to the individual CG0070, wherein CG0070 is administered weekly at a dose of about $1\times10^8$ to about $1\times10^{14}$ viral particles (such as about $1\times10^{12}$ viral particles) for about 6 weeks. In some embodiments, the method further comprises administering to the individual a transduction enhancing agent (such as DDM) prior to the administration of CG0070. In some embodiments, CG0070 is not administered in conjunction with an immune checkpoint modulator. In some embodiments, CG0070 is administered as a single therapeutic agent. In some embodiments, the individual is unresponsive or has disease reoccurrence subsequent to BCG treatment. In some embodiments, the individual has refused or is ineligible for cystectomy (such as radical cystectomy).

In some embodiments, the individual has refused cystectomy, such as partial cystectomy or radical cystectomy. In some embodiments, the individual is ineligible for cystectomy, such as partial cystectomy or radical cystectomy. In some embodiments, the individual is less tolerable to cystectomy. In some embodiments, the individual is medically inoperable. In some embodiments, the individual has previously received a full course of external-beam radiotherapy, and has bulky residual disease. In some embodiments, the individual has previously received a bladder-preserving therapy. In some embodiments, the individual is an elderly patient. In some embodiments, the individual cannot tolerate cystectomy because of age. In some embodiments, the individual is at least about any of 60, 65, 70, 75, 80, 85, 90, 95 years old or older. In some embodiments, the individual has renal deficiency or renal failure. According to NCCN Guidelines for Bladder Cancer, partial cystectomy is indicated for T2 muscle invasive disease with solitary lesion in location amenable to segmental resection with adequate margins, and no carcinoma in situ is determined by random biopsy. Radical cystectomy or cystoprostatectomy is indicated for residual high-grade T1, and muscle-invasive disease. Cystectomy is normally given within 3 months of diagnosis if no therapy is given to the patient. Additionally, Cystectomy is indicated for recurrent or persistent bladder cancer at Ta, T1 or CIS stage, after TURBT or BCG treatment.

In some embodiments, the individual is ineligible for radical cystectomy under the National Comprehensive Cancer Network (NCCN) guidelines. For example, the individual may be unfit for curative therapy due to frailty. Prior to the present methods, such individuals typically received palliative radiation without chemotherapy (3.5 Gy/fraction—10 treatments; or 7 Gy/fraction—7 treatments; TURBT; or no treatment).

In some embodiments, the individual cannot tolerate radical cystectomy based upon the American Society of Anesthesiology (ASA) guidelines. For example the individual who cannot tolerate radial cystectomy may be deemed medically unfit for surgery requiring general or epidural anesthesia.

In other embodiments, the individual may lack operative post-operative care infrastructure or personal as determined by the Comprehensive Geriatric Assessment provided by the American Society of Anesthesiologists. Under these guidelines, an individual is deemed frail if he or she shows abnormal independent activities of daily living, severe malnutrition, cognitive impairment, or comorbidities cumulative illness rating scale for geriatrics (CISR-G) grades 3-4.

Thus, in some embodiments, there is provided a method of treating an individual having bladder cancer, comprising intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule, and wherein the individual has refused or is ineligible for cystectomy (such as radical cystectomy). In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the method further comprises administering to the individual a transduction enhancing agent (such as DDM) prior to the administration of the oncolytic virus. In some embodiments, the oncolytic virus is administered at a dose of about $1\times10^8$ to about $1\times10^{14}$ viral particles (such as about $1\times10^{12}$ viral particles). In some embodiments, the oncolytic virus is administered weekly. In some embodiments, the oncolytic virus is administered for about 1 week to about 6 weeks (such as about 3 weeks or about 6 weeks).

The methods of the present invention also provide important and significant treatment benefits compared to standard therapeutic regimens that call for removal of the bladder. The present invention also has the advantage of being useful as a bladder sparing protocol for individuals who are eligible for a cystectomy, but elect not to have a cystectomy. The present methods result in a greatly improved quality of life for individuals, who may be able to retain their bladder after having bladder cancer, compared to the presently available treatments.

Accordingly, in some embodiments, there is provided herein is a bladder sparing method comprising intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule, and wherein the individual has refused or is ineligible for cystectomy (such as radical cystectomy). In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the method further comprises administering to the individual a transduction enhancing agent (such as DDM) prior to the administration of the oncolytic virus. In some embodiments, the oncolytic virus is administered at a dose of about $1\times10^8$ to about $1\times10^{14}$ viral particles (such as about $1\times10^{12}$ viral particles). In some embodiments, the oncolytic virus is administered weekly. In some embodiments, the oncolytic virus is administered for about 1 week to about 6 weeks (such as about 3 weeks or about 6 weeks).

In some embodiments, the individual has been previously treated for bladder cancer (also referred to as the "prior therapy"). In some embodiments, the prior therapy comprises one or more (such as 1, 2, 3, 4, 5, or more) treatment modalities, including, but are not limited to surgery (such as transurethral resection of bladder tumor, or partial cystectomy), intravesical therapy (such as BCG or intravesical chemotherapy), radiation therapy, chemotherapy, immunotherapy, and combinations thereof.

In some embodiments, the present methods are especially suited for individuals who relapse after BCG therapy after at least 3, 4, 5, 6, 7, 8, 9, 10, 11, or 12 months. In some embodiments, the methods are especially suitable for individuals who relapse at least 9 months after receiving BCG therapy. In some embodiments, the individual has CIS.

In some embodiments, the individual has been previously treated with a standard therapy for bladder cancer. In some embodiments, the individual has been previously treated with a standard therapy for non-invasive papillary carcinoma. In some embodiments, the individual has been previously treated with a standard therapy for bladder CIS. In some embodiments, the prior standard therapy is an intravesical therapy, such as intravesical chemotherapy or intravesical immunotherapy. In some embodiments, the prior standard therapy is treatment with mitomycin C. In some embodiments, the prior standard therapy is treatment with interferon (such as interferon-α). In some embodiments, the prior standard therapy is treatment with platinum-based agents. In some embodiments, the prior standard therapy is treatment with mitomycin and thiotepa. In some embodiments, the prior standard therapy is treatment with cisplatin, doxorubicin, gemcitabine, and valrubicin. In some embodiments, the prior standard therapy is BCG treatment.

In some embodiments, the individual has bladder CIS in remission, progressive bladder CIS, persistent bladder CIS, or recurrent bladder CIS. In some embodiments, the individual is resistant to treatment of bladder CIS with other agents (such as BCG, or chemotherapy agent). In some embodiments, the individual is initially responsive to treatment of bladder CIS with other agents (such as BCG, or chemotherapy agent) but has progressed after treatment. In some embodiments, the individual has persistent or recurrent bladder CIS after receiving TURBT. In some embodiments, the individual has persistent or recurrent bladder CIS after receiving an intravesical therapy, such as intravesical BCG or intravesical chemotherapy (e.g., mitomycin C). In some embodiments, the individual has persistent or recurrent bladder CIS after receiving at least 2 consecutive cycles or an intravesical therapy, and/or at least two intravesical agents (e.g., intravesical BCG followed by intravesical mitomycin C). In some embodiments, the individual has persistent or recurrent bladder CIS after receiving a combination of TURBT and one or more intravesical therapy.

In some embodiments, the individual has recurrent bladder CIS (such as pure CIS) after a prior therapy (such as prior standard therapy, for example intravesical BCG). For example, the individual may be initially responsive to the treatment with the prior therapy, but develops bladder CIS after about any of about 2, 3, 4, 5, 6, 7, 8, 9, 10, 11, 12, 24, 36, 48, or 60 months upon the cessation of the prior therapy.

In some embodiments, the individual has previously received BCG treatment. In some embodiments, the individual has previously received at least one (such as at least about any one of 1, 2, 3, 4, 5, 6, or more) course of intravesical BCG treatment. In some embodiments, the intravesical BCG treatment comprises weekly intravesical instillation of BCG for at least about 4 weeks, such as at least about any one of 5, 6, 7, 8, 9, or more weeks. In some embodiments, the individual has previously received an induction course of intravesical BCG treatment (such as about 4 to about 9, e.g., about 6 weekly BCG administration). In some embodiments, the individual has previously received an induction course and at least one maintenance course of intravesical BCG treatment. In some embodiments, the individual has previously received a 6-233 k induction course of BCG followed by maintenance with three weekly instillations at about any one or more of months 3, 6, 12, 18, 24, 30 and 36. In some embodiments, the individual has been on maintenance intravesical BCG treatment for at least about 3 months, such as at least about any one of 3, 4, 5, 6, 7, 8, 9, 10, 11, 12, 18, 24, 30, 36 months or longer. In some embodiments, the individual has received BCG treatment within about any one of 12, 11, 10, 9, 8, 7, 6, 5, 4, 3, 2, or 1 month before receiving the viral treatment of the present application. In some embodiments, the individual has severe adverse effects after intravesical BCG treatment. In some embodiments, the individual has bacteriuria, persistent gross hematuria, persistent severe local symptoms, or systemic symptoms. In some embodiments, the individual cannot tolerate the intravesical BCG treatment even after dose reduction.

In some embodiments, the individual has failed the BCG treatment. In some embodiments, the individual has failed the BCG treatment within about any one of 24, 22, 20, 18, 16, 14, 12, 11, 10, 9, 8, 7, 6, 5, 4, 3, 2, or 1 month after the last administration of BCG. In some embodiments, the individual has failed the induction course of intravesical BCG treatment. In some embodiments, the individual has failed the BCG treatment during or after the maintenance course(s).

In some embodiments, the individual is unresponsive to the BCG treatment. In some embodiments, the individual had partial response to the BCG treatment. In some embodiments, the individual could not tolerate the adverse effects of the BCG treatment. In some embodiments, the individual has disease reoccurrence subsequent to the BCG treatment. In some embodiments, the individual has disease reoccurrence after no more than about any one of 24, 22, 20, 18, 16, 14, 12, 11, 10, 9, 8, 7, 6, 5, 4, 3, 2, or 1 month after the last administration of BCG (such as BCG induction or BCG maintenance). In some embodiments, the individual has disease progression despite receiving maintenance courses of the BCG treatment. In some embodiments, the individual had bladder CIS prior to the BCG treatment. In some embodiments, the individual did not have bladder CIS prior to the BCG treatment. In some embodiments, the individual had papillary tumors (such as stage Ta or T1) prior to the BCG treatment. In some embodiments, the individual had both bladder CIS and papillary tumors (such as stage Ta or T1) prior to the BCG treatment.

Thus, in some embodiments, there is provided a method of treating BCG-unresponsive non-muscle-invasive bladder cancer (such as BCG-unresponsive bladder CIS) in an individual, comprising intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the individual only has bladder CIS. In some embodiments, the individual has refused or is ineligible for cystectomy (such as radical cystectomy). In some embodiments, the method further comprises administering to the individual a transduction enhancing agent (such as DDM) prior to the administration of the oncolytic virus. In some embodiments, the oncolytic virus is administered at a dose of about $1 \times 10^8$ to about $1 \times 10^{14}$ viral particles (such as about $1 \times 10^{12}$ viral particles). In some embodiments, the oncolytic virus is administered weekly. In some embodiments, the oncolytic virus is administered for about 1 week to about 6 weeks (such as about 6 weeks).

In some embodiments, there is provided a method of treating an individual having bladder CIS, comprising intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule, and wherein the individual has disease reoccurrence subsequent to BCG treatment. In some embodiments, the oncolytic virus is not administered in conjunction with an immune checkpoint modulator. In some embodiments, the oncolytic virus comprises a tumor-selective promoter. In some embodiments, the oncolytic virus is administered as a single therapeutic agent. In some embodiments, the individual only has bladder CIS. In some embodiments, the individual has refused or is ineligible for cystectomy (such as radical cystectomy). In some embodiments, the method further comprises administering to the individual a transduction enhancing agent (such as DDM) prior to the administration of the oncolytic virus. In some embodiments, the oncolytic virus is administered at a dose of about $1 \times 10^8$ to about $1 \times 10^{14}$ viral particles (such as about $1 \times 10^{12}$ viral particles). In some embodiments, the oncolytic virus is administered weekly. In some embodiments, the oncolytic virus is administered for about 1 week to about 6 weeks (such as about 3 weeks or about 6 weeks).

Endpoints

In some embodiments, the method prevents progression of the bladder cancer in the individual. In some embodiments, the method prevent progression of the non-muscle invasive bladder cancer to muscle invasive bladder cancer by at least about any one of 3, 6, 9, 12, 18, 24, 30, 36, 42, 48, 54, 60 or more months.

In some embodiments, there is provided a method of preventing disease progression in an individual having bladder cancer, comprising intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the individual is unresponsive or has disease reoccurrence subsequent to BCG treatment. In some embodiments, the individual has refused or is ineligible for cystectomy (such as radical cystectomy). In some embodiments, the method further comprises administering to the individual a transduction enhancing agent (such as DDM) prior to the administration of the oncolytic virus. In some embodiments, the oncolytic virus is administered at a dose of about $1 \times 10^8$ to about $1 \times 10^{14}$ viral particles (such as about $1 \times 10^{12}$ viral particles). In some embodiments, the oncolytic virus is administered weekly. In some embodiments, the oncolytic virus is administered for about 1 week to about 6 weeks (such as about 3 weeks or about 6 weeks). In some embodiments, the bladder cancer is CIS, CIS+Ta, CIS+T1, Ta, or T1 grade bladder cancer.

In some embodiments, the method inhibits growth or reduces the size of the bladder cancer. In some embodiments, the size of the bladder cancer is reduced for at least about 10% (including for example at least about any of 20%, 30%, 40%, 60%, 70%, 80%, 90%, or 100%).

In some embodiments, there is provided a method of inhibiting tumor growth or reducing tumor size in an individual having bladder cancer, comprising intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the individual is unresponsive or has disease reoccurrence subsequent to BCG treatment. In some embodiments, the individual has refused or is ineligible for cystectomy (such as radical cystectomy). In some embodiments, the method further comprises administering to the individual a transduction enhancing agent (such as DDM) prior to the administration of the oncolytic virus. In some embodiments, the oncolytic virus is administered at a dose of about $1 \times 10^8$ to about $1 \times 10^{14}$ viral particles (such as about $1 \times 10^{12}$ viral particles). In some embodiments, the oncolytic virus is administered weekly. In some embodiments, the oncolytic virus is administered for about 1 week to about 6 weeks (such as about 3 weeks or about 6 weeks). In some embodiments, the bladder cancer is CIS, CIS+Ta, CIS+T1, Ta, or T1 grade bladder cancer.

In some embodiments, the method causes disease remission (partial or complete) in the individual. In some embodiments, the individual has disease remission for at least about any one of 2, 3, 4, 5, 6, 12, 24, or more months.

In some embodiments, there is provided a method of causing disease remission (such as partial or complete remission) in an individual having bladder CIS (such as pure CIS), comprising intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the individual is unresponsive or has disease reoccurrence subsequent to BCG treatment. In some embodiments, the individual has refused or is ineligible for cystectomy (such as radical cystectomy). In some embodiments, the method further comprises administering to the individual a transduction enhancing agent (such as DDM) prior to the administration of the oncolytic virus. In some embodiments, the oncolytic virus is administered at a dose of about $1 \times 10^8$ to about $1 \times 10^{14}$ viral particles (such as about $1 \times 10^{12}$ viral particles). In some embodiments, the oncolytic virus is administered weekly. In some embodiments, the oncolytic virus is administered for about 1 week to about 6 weeks (such as about 3 weeks or about 6 weeks).

In some embodiments, the method inhibits tumor metastasis in the individual. In some embodiments, at least about 10% (including for example at least about any of 20%, 30%, 40%, 60%, 70%, 80%, 90%, or 100%) metastasis is inhibited. In some embodiments, a method of inhibiting metastasis to lymph node is provided. In some embodiments, a method of inhibiting metastasis to the lung is provided. Metastasis can be assessed by any known methods in the art, such as by blood tests, bone scans, x-ray scans, CT scans, PET scans, and biopsy.

In some embodiments, there is provided a method of inhibiting tumor metastasis in an individual having bladder cancer, comprising intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the individual is unresponsive or has disease reoccurrence subsequent to BCG treatment. In some embodiments, the individual has refused or is ineligible for cystectomy (such as radical cystectomy). In some embodiments, the method further comprises administering to the individual a transduction enhancing agent (such as DDM) prior to the administration of the oncolytic virus. In some embodiments, the oncolytic virus is administered at a dose of about $1 \times 10^8$ to about $1 \times 10^{14}$ viral particles (such as about $1 \times 10^{12}$ viral particles). In some embodiments, the oncolytic virus is administered weekly. In some embodiments, the oncolytic virus is administered for about 1 week to about 6 weeks (such as about 3 weeks or about 6 weeks). In some embodiments, the bladder cancer is CIS, CIS+Ta, CIS+T1, Ta, or T1 grade bladder cancer.

In some embodiments, the method prolongs survival (such as disease free survival, progression-free survival, or cystectomy-free survival) in the individual. In some embodiments, the survival is prolonged for at least about 2, 3, 4, 5, 6, 12, 24, or more months.

In some embodiments, there is provided a method of prolonging survival (such as disease free survival, progression-free survival, or cystectomy-free survival) in an individual having bladder cancer, comprising intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the individual is unresponsive or has disease reoccurrence subsequent to BCG treatment. In some embodiments, the individual has refused or is ineligible for cystectomy (such as radical cystectomy). In some embodiments, the method further comprises administering to the individual a transduction enhancing agent (such as DDM) prior to the administration of the oncolytic virus. In some embodiments, the oncolytic virus is administered at a dose of about $1 \times 10^8$ to about $1 \times 10^{14}$ viral particles (such as about $1 \times 10^{12}$ viral particles). In some embodiments, the oncolytic virus is administered weekly. In some embodiments, the oncolytic virus is administered for about 1 week to about 6 weeks (such as about 3 weeks or about 6 weeks). In some embodiments, the bladder cancer is CIS, CIS+Ta, CIS+T1, Ta, or T1 grade bladder cancer.

In some embodiments, the method improves quality of life in the individual. In some embodiments, the individual does not need a cystectomy (such as partial cystectomy or radical cystectomy) after receiving the viral therapy of the present application for at least about any one of 3, 6, 9, 12, 18, 24, 30, 36, 42, 48, 54, 60 or more months. In some embodiments, because the method of the present application delays or obviates the need for radical cystectomy in the individual, the individual enjoys improved quality of life compared to other bladder CIS patients because the individual does not suffer from undesirable side effects due to reconstructive surgery after radical cystectomy.

In some embodiments, there is provided a method of improving quality of life in an individual having bladder CIS (such as pure CIS), comprising intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the individual is unresponsive or has disease reoccurrence subsequent to BCG treatment. In some embodiments, the individual has refused or is ineligible for cystectomy (such as radical cystectomy). In some embodiments, the method further comprises administering to the individual a transduction enhancing agent (such as DDM) prior to the administration of the oncolytic virus. In some embodiments, the oncolytic virus is administered at a dose of about $1\times10^8$ to about $1\times10^{14}$ viral particles (such as about $1\times10^{12}$ viral particles). In some embodiments, the oncolytic virus is administered weekly. In some embodiments, the oncolytic virus is administered for about 1 week to about 6 weeks (such as about 3 weeks or about 6 weeks). In some embodiments, the bladder cancer is CIS, CIS+Ta, CIS+T1, Ta, or T1 grade bladder cancer.

In some embodiments, there is provided a method of treating bladder cancer in an individual without subjecting the individual to cystectomy (such as radical cystectomy), comprising intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the individual is unresponsive or has disease reoccurrence subsequent to BCG treatment. In some embodiments, the individual has refused or is ineligible for cystectomy (such as radical cystectomy). In some embodiments, the method further comprises administering to the individual a transduction enhancing agent (such as DDM) prior to the administration of the oncolytic virus. In some embodiments, the oncolytic virus is administered at a dose of about $1\times10^8$ to about $1\times10^{14}$ viral particles (such as about $1\times10^{12}$ viral particles). In some embodiments, the oncolytic virus is administered weekly. In some embodiments, the oncolytic virus is administered for about 1 week to about 6 weeks (such as about 3 weeks or about 6 weeks). In some embodiments, the bladder cancer is CIS, CIS+Ta, CIS+T1, Ta, or T1 grade bladder cancer.

In some embodiments, there is provided a bladder-preserving method of treating bladder CIS (such as pure CIS) in an individual, comprising intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the individual is unresponsive or has disease reoccurrence subsequent to BCG treatment. In some embodiments, the individual has refused or is ineligible for cystectomy (such as radical cystectomy). In some embodiments, the method further comprises administering to the individual a transduction enhancing agent (such as DDM) prior to the administration of the oncolytic virus. In some embodiments, the oncolytic virus is administered at a dose of about $1\times10^8$ to about $1\times10^{14}$ viral particles (such as about $1\times10^{12}$ viral particles). In some embodiments, the oncolytic virus is administered weekly. In some embodiments, the oncolytic virus is administered for about 1 week to about 6 weeks (such as about 3 weeks or about 6 weeks). In some embodiments, the bladder cancer is CIS, CIS+Ta, CIS+T1, Ta, or T1 grade bladder cancer.

Treatment Regimens

The intravesical administration of the oncolytic virus provide a unique opportunity of a relatively convenient yet effective intravesical tumor exposure to the oncolytic virus, as well as a potentially reduced toxicity to other tissues. Suitable dosages for the oncolytic virus depend on factors such as the nature of the oncolytic virus, type of the bladder carcinoma in situ being treated, and routes of administration. As used herein, "particles" as related to an oncolytic virus mean the collective number of physical singular units of the oncolytic virus. This number can be converted to, or is equivalent to, another number meaning infectious titer units, e.g., plaque forming unit (pfu) or international unit, by infectivity assays as known in the art. In some embodiments, the oncolytic virus is administered at a dose of about any one of $1\times10^5$ particles, $1\times10^6$ particles, $1\times10^7$ particles, $1\times10^8$ particles, $1\times10^9$ particles, $1\times10^{10}$ particles, $2\times10^{10}$ particles, $5\times10^{10}$ particles, $1\times10^{11}$ particles, $2\times10^{11}$ particles, $5\times10^{11}$ particles, $1\times10^{12}$ particles, $2\times10^{12}$ particles, $5\times10^{12}$ particles, $1\times10^{13}$ particles, $2\times10^{13}$ particles, $5\times10^{13}$ particles, $1\times10^{14}$ particles, or $1\times10^{15}$ particles. In some embodiments, the oncolytic virus is administered at a dose of any one of about $1\times10^5$ particles to about $1\times10^6$ particles, about $1\times10^6$ particles to about $1\times10^7$ particles, about $1\times10^7$ particles to about $1\times10^8$ particles, about $1\times10^8$ particles to about $1\times10^9$ particles, about $1\times10^9$ particles to about $1\times10^{10}$ particles, about $1\times10^{10}$ particles to about $1\times10^{11}$ particles, about $1\times10^{11}$ particles to about $5\times10^{11}$ particles, about $5\times10^{11}$ particles to about $1\times10^{12}$ particles, about $1\times10^{12}$ particles to about $2\times10^{12}$ particles, about $2\times10^{12}$ particles to about $5\times10^{12}$ particles, about $5\times10^{12}$ particles to about $1\times10^{13}$ particles, about $1\times10^{13}$ particles to about $1\times10^{14}$ particles, or about $1\times10^{14}$ particles to about $1\times10^{15}$ particles.

In some embodiments, the oncolytic virus is administered daily. In some embodiments, the oncolytic virus is administered is administered at least about any one of 1×, 2×, 3×, 4×, 5×, 6×, or 7× (i.e., daily) a week. In some embodiments, the oncolytic virus is administered weekly. In some embodiments, the oncolytic virus is administered weekly without break; weekly, two out of three weeks; weekly three out of four weeks; once every two weeks; once every 3 weeks; once every 4 weeks; once every 6 weeks; once every 8 weeks, monthly, or every two to 12 months. In some embodiments, the intervals between each administration are less than about any one of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any one of 1 month, 2 months, 3 months, 4 months, 5 months, 6 months, 8 months, or 12 months. In some embodiments, there is no break in the dosing schedule. In some embodiments, the interval between each administration is no more than about a week.

The administration of the oncolytic virus can be over an extended period of time, such as from about a month up to about seven years. In some embodiments, the oncolytic virus is administered over a period of at least about any one of 1, 2, 3, 4, 5, 6, 7, 8, 9, 10, 11, 12, 18, 24, 30, 36, 48, 60, 72, or 84 months. In some embodiments, the oncolytic virus is administered over a period of at least 4 weeks or 6 weeks. In some embodiments, the oncolytic virus is administered weekly for four weeks every 3 months. In some embodiments, the oncolytic virus is administered weekly for 6 weeks every 3 months.

In some embodiments, each treatment course comprises weekly administration of the oncolytic virus for about 3 or about 6 weeks. In some embodiments, the interval between each course of treatment is at least about any one of 1, 2, 3, 4, 5, 6, or more months. In some embodiments, the interval between each course of treatment is no more than about any one of 6, 5, 4, 3, 2, 1 months or less. In some embodiments, the treatment course is repeated at least once, such as at least about any of 1, 2, 3, 4, 5, 6, or more times. In some embodiments, the individual is treated with an initial course of the oncolytic virus, followed by a maintenance course. In some embodiments, the initial course and the maintenance course have the same dose and schedule. In some embodiments, the initial course and the maintenance course have different doses and/or schedules.

In some embodiments, the oncolytic virus is administered by instillation as a solution via a catheter. In some embodiments, the total volume of the solution used for the intravesical installation is about any of 1 mL, 10 mL, 50 mL, 75 mL, 100 mL, 125 mL, 150 mL, 200 mL, 250 mL, 300 mL, 400 mL or 500 mL. In some embodiments, the total volume of the solution used for the intravesical installation is any of about 1 mL to about 10 mL, about 10 mL to about 50 mL, about 50 mL to about 75 mL, about 75 mL to about 100 mL, about 100 mL to about 125 mL, about 75 mL to about 125 mL, about 100 mL to about 150 mL, about 150 mL to about 200 mL, about 200 mL to about 300 mL, about 300 mL to about 400 mL, about 400 mL to about 500 mL, about 50 mL to about 500 mL, about 50 mL to about 250 mL, or about 100 mL to about 250 mL.

In some embodiments, the oncolytic virus is administered at a dose of about $1 \times 10^8$ to about $1 \times 10^{15}$ particles (such as about $1 \times 10^{11}$ to about $1 \times 10^{14}$ particles, for example about $1 \times 10^{12}$ particles). In some embodiments, the oncolytic virus is administered at a volume of about 50 to about 500 mL (such as about 100 mL) by instillation. In some embodiments, the oncolytic virus is administered at a dose of about $1 \times 10^{12}$ in about 50 mL.

The solution of the oncolytic virus may be retained in the bladder for a certain amount of time before voiding, in order to achieve uniform distribution or sufficient exposure of the oncolytic virus among the bladder tumor cells. In some embodiments, the solution is retained in the bladder of the individual for at least about any of 5 minutes, 10 minutes, 15 minutes, 20 minutes, 30 minutes, 45 minutes, 1 hour, 2 hours, or more. In some embodiments, the solution is retained in the bladder of the individual for any of about 5 minutes to about 10 minutes, about 10 minutes to about 15 minutes, about 10 minutes to about 20 minutes, about 20 minutes to about 30 minutes, about 30 minutes to about 45 minutes, about 45 minutes to about 50 minutes, about 50 minutes to about 1 hour, about 5 minutes to about 15 minutes, about 10 minutes to about 30 minutes, about 30 minutes to about 1 hour, or about 1 hour to about 2 hours. In some embodiments, the oncolytic virus (e.g., CG0070) is retained in the bladder of the individual for about 45 minutes to about 50 minutes. In some embodiments, the efficiency of the intravesical administration of the oncolytic virus is further enhanced by a pretreatment comprising intravesical administration of an effective amount of a transduction enhancing agent, such as DDM.

The methods described herein may further comprise a step of intravesically administering to the individual a pretreatment composition prior to the administration of the oncolytic virus. In some embodiments, the pretreatment composition comprises a transduction enhancing agent, such as N-Dodecyl-β-D-maltoside (DDM). DDM is a nonionic surfactant comprised of a maltose derivatized with a single twelve-carbon chain, and acts as a mild detergent and solubilizing agent. It has been used as a food additive and is known to enhance mucosal surface permeation in rodents, probably due to its effect on membrane associated GAG and tight junctions.

In some embodiments, there is provided a method of treating bladder cancer in an individual, comprising: (1) intravesically administering to the individual a transduction enhancing agent (such as DDM); and subsequently (2) intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the individual is unresponsive or has disease reoccurrence subsequent to BCG treatment. In some embodiments, the individual has refused or is ineligible for cystectomy (such as radical cystectomy). In some embodiments, the oncolytic virus is administered at a dose of about $1 \times 10^8$ to about $1 \times 10^{14}$ viral particles (such as about $1 \times 10^{12}$ viral particles). In some embodiments, the oncolytic virus is administered weekly. In some embodiments, the oncolytic virus is administered for about 1 week to about 6 weeks (such as about 3 or about 6 weeks). In some embodiments, the bladder cancer is CIS, CIS+Ta, CIS+T1, Ta, or T1 grade bladder cancer. In some embodiments, the individual does not receive a resection prior to administration of oncolytic virus. In some embodiments, the individual has Ta or T1 bladder cancer and has not received a transurothelial resection of bladder tumor (TURBT). In some embodiments, the bladder cancer is Ta or T1 non-resectable bladder cancer. In some embodiments, a saline wash is performed prior to intravesically administering to the individual a transduction enhancing agent.

In some embodiments, provided herein is a method of treating bladder cancer (such as CIS bladder cancer or Ta or T1 grade bladder cancer without TURBT) comprising: (1) administering an intravesicular saline wash (2) administering an intravesicular wash with a transduction enhancing agent (such as DDM); (3) administering to the individual an intravesicular instillation of a transduction enhancing agent (such as DDM); and subsequently (4) intravesically administering to the individual an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule. In some embodiments, the oncolytic virus comprises a tumor-selective promoter. In some embodiments, the oncolytic virus is not administered in conjunction with an immune checkpoint modulator. In some embodiments, the oncolytic virus is administered as a single therapeutic agent. In some embodiments, the individual is unresponsive or has disease reoccurrence subsequent to BCG treatment. In some embodiments, the individual has refused or is ineligible for cystectomy (such as radical cystectomy). In some embodiments, the oncolytic virus is administered at a dose of about $1 \times 10^8$ to about $1 \times 10^{14}$ viral particles (such as about $1 \times 10^{12}$ viral particles). In some embodiments, the oncolytic virus is administered weekly. In some embodiments, the oncolytic virus is administered for about 1 week to about 6 weeks (such as about 3 or about 6 weeks). In some embodiments, the bladder cancer is CIS, CIS+Ta, CIS+T1, Ta, or T1 grade bladder cancer. In some embodiments, the individual has Ta or T1 bladder cancer and has not received a transurothelial resection of bladder tumor (TURBT). In some embodiments, the bladder cancer is Ta or T1 non-resectable bladder cancer. In some embodiments, the individual does not receive a resection prior to administration of oncolytic virus. In some embodiments the transduction enhancing agent is retained in the bladder for 12 to 15 minutes during the intravesicular instillation. In some embodiments, a saline rinse is administered following intravesicular instillation of a transduction enhancing agent and administering an oncolytic virus.

The pretreatment composition is administered intravesically. In some embodiments, the pretreatment composition comprises a solution of the transduction enhancing agent (such as DDM). Suitable concentration of the pretreatment composition (such as DDM solution) include, but are not limited to, about any one of 0.01%, 0.05%, 0.1%, 0.2%, 0.3%, 0.4%, 0.5%, 1%, 2%, 3%, 4%, or 5% of the transducing enchanting agent (such as DDM). In some embodiments, the pretreatment composition comprises any of about 0.01% to about 0.05%, about 0.05% to about 0.1%, about 0.1% to about 0.5%, about 0.5% to about 1%, about 1% to about 2%, about 2% to about 3%, about 3% to about 4%, about 4% to about 5%, about 0.01% to about 1%, about 0.05% to about 2%, about 1% to about 5%, or about 0.1% to about 5% of the transduction enhancing agent (such as DDM).

Suitable dosages for the pretreatment composition (such as DDM) include, but are not limited to, about any of 0.1 mg/kg, 0.5 mg/kg, 1 mg/kg, 1.5 mg/kg, 2 mg/kg, 2.5 mg/kg, 5 mg/kg, 10 mg/kg, 25 mg/kg, 50 mg/kg, 100 mg/kg, 150 mg/kg, 200 mg/kg, 250 mg/kg, 300 mg/kg, 400 mg/kg, 500 mg/kg, 0.1 mg/kg to 0.5 mg/kg, 0.5 mg/kg to 1 mg/kg, 1 mg/kg to 2 mg/kg, 2 mg/kg to 5 mg/kg, 5 mg/kg to 10 mg/kg, 10 mg/kg to 25 mg/kg, 25 mg/kg to 50 mg/kg, 50 mg/kg to 100 mg/kg, 100 mg/kg to 150 mg/kg, 150 mg/kg to 200 mg/kg, 200 mg/kg to 250 mg/kg, 250 mg/kg to 500 mg/kg, or 0.5 mg/kg to about 5 mg/kg. In some embodiments, a suitable dosage for the pretreatment composition is about any one of 0.1 g, 0.2 g, 0.5 g, 0.75 g, 1 g, 1.5 g, 2 g, 2.5 g, 5 g, or 10 g of the transduction enhancing agent (such as DDM).

In some embodiments, the pretreatment step is carried out by contacting the luminal surface of the bladder in the individual with the pretreatment composition prior to the administration of the oncolytic virus. For example, the pretreatment composition may comprise about 0.01% to about 0.5% (such as 0.05 to about 0.2%, for example about 0.1%) of the transduction enhancing agent (such as DDM). In some embodiments, the total volume of the pretreatment composition (such as DDM) is about 10 mL to about 1000 mL (such as about 10 mL to about 100 mL, about 100 mL to about 500 mL, or about 500 mL to about 1000 mL). In some embodiments, the pretreatment composition comprises about 0.1% DDM. In some embodiments, a suitable dosage for the pretreatment composition is about any one of 0.1 g, 0.2 g, 0.5 g, 0.75 g, 1 g, 1.5 g, 2 g, 2.5 g, 5 g, or 10 g of the transduction enhancing agent (such as DDM). In some embodiments, the effective amount of the pretreatment composition is about 1 g of DDM (e.g., 100 mL of 0.1% DDM solution).

In some embodiments, the pretreatment composition (such as DDM) is administered immediately (such as no more than 5 minutes) prior to the administration of the oncolytic virus. In some embodiments, the pretreatment composition (such as DDM) is administered no more than about any of 5 minutes, 10 minutes, 15 minutes, 20 minutes, 30 minutes, 45 minutes, 1 hour, 90 minutes, 2 hours, 3 hours or 4 hours before the administration of the oncolytic virus. In some embodiments, the pretreatment composition (such as DDM) is administered no more than about 2 hours before the administration of the oncolytic virus. In some embodiments, the pretreatment composition (such as DDM solution) is retained in the bladder for at least about any one of 5 minutes, 10 minutes, 15 minutes, or 20 minutes. In some embodiments, the pretreatment composition (such as DDM solution) is retained in the bladder for any of about 5 minutes to about 10 minutes, about 10 minutes to about 15 minutes, about 12 minutes to about 15 minutes, about 15 minutes to about 20 minutes, or about 10 minutes to about 20 minutes. In some embodiments, the pretreatment composition (such as DDM solution) is retained in the bladder for about 12 minutes to about 15 minutes.

In some embodiments, the pretreatment step is carried out by contacting the luminal surface of the bladder in the individual with the pretreatment composition prior to the administration of the oncolytic virus. In some embodiments, the method further comprises washing the luminal surface of the bladder contact with the pretreatment composition. In some embodiments, the method further comprises washing the luminal surface of the bladder after contacting the bladder with the pretreatment composition prior to the administration of the oncolytic virus.

In some embodiments, the pretreatment step comprises intravesically instilling 75 mL or 100 mL of a pretreatment composition (such as a DDM solution).

In some embodiments, the individual is a human individual. In some embodiments, the individual being treated for bladder carcinoma in situ has been identified as having one or more of the conditions described herein. Identification of the conditions as described herein by a skilled physician is routine in the art (e.g., via blood tests, X-rays, ultrasound, CT scans, PET scans, PET/CT scans, Mill scans, PET/MRI scans, nuclear medicine radioisotope scans, endoscopy, biopsy, angiography, CT-angiography, etc.) and may also be suspected by the individual or others, for example, due to tumor growth, hemorrhage, ulceration, pain, enlarged lymph nodes, cough, jaundice, swelling, weight loss, cachexia, sweating, anemia, paraneoplastic phenomena, thrombosis, etc. In some embodiments, the individual is selected for any one of the treatment methods described herein based on any one or more of a number of risk factors and/or diagnostic approaches appreciated by the skilled artisan, including, but not limited to, genetic profiling, family history, medical history (e.g., appearance of related conditions and viral infection history), lifestyle or habits.

Oncolytic Virus

The methods and compositions described herein are related to oncolytic viruses, for example, oncolytic adenovirus. The oncolytic virus may be a naturally occurring virus, or a genetically modified virus, for example an attenuated virus, and/or a virus with additional favorable features (e.g., preferential replication in cancer cells, or encoding an immune-related molecule).

Exemplary viruses that are suitable for use in the present invention include, but are not limited to, adenovirus, for example, H101 ONCOCRINE®), CG-TG-102 (Ad5/3-D24-GM-CSF), and CG0070; herpes simplex virus, for example, Talimogene laherparapvec (T-VEC) and HSV-1716 (SEPREHVIR®); reo virus, for example, REOLYSIN®; vaccinia virus, for example, JX-594; Seneca valley virus, for example, NTX-010 and SVV-001; newcastle disease virus, for example, NDV-NS1 and GL-ONC1; polio virus, for example, PVS-RIPO; measles virus, for example, MV-NIS; coxsackie virus, for example, CAVATAK™; vesicular stomatitis virus; maraba and rhabdoviruses; parvovirus and mumps virus.

In some embodiments, the oncolytic virus is a wild type oncolytic virus. In some embodiments, the oncolytic virus is genetically modified. In some embodiments, the oncolytic virus is attenuated (for example through multiple passages, inactivation or genetic modification). In some embodiments, the oncolytic virus is replication competent. In some embodiments, the oncolytic virus preferentially replicates in a cancer cell, such as a cancer cell defective in the Rb pathway.

In some embodiments, the oncolytic virus (such as oncolytic adenovirus) comprises a viral vector comprising a tumor cell-specific promoter operably linked to a viral gene essential for replication of the oncolytic virus. In some embodiments, the tumor-specific promoter is an E2F-1 promoter, such as a human E2F-1 promoter or an E2F-1 promoter comprising the nucleotide sequence set forth in SEQ ID NO:1 as shown below. In some embodiments, the viral gene essential for replication of the oncolytic virus is selected from the group consisting of E1A, E1B, and E4.

In some embodiments, the oncolytic virus (such as oncolytic adenovirus) comprises a viral vector comprising a tumor-selective promoter operably linked to a viral gene essential for replication of the oncolytic virus. In some embodiments, the tumor-selective promoter is an E2F-1 promoter, such as a human E2F-1 promoter or an E2F-1 promoter comprising the nucleotide sequence set forth in SEQ ID NO:1 as shown below. In some embodiments, the viral gene essential for replication of the oncolytic virus is selected from the group consisting of E1A, E1B, and E4.

```
                                                SEQ ID NO: 1
(E2F-1 promoter)
gggcccaaaattagcaagtgaccacgtggttctgaagccagtggcctaag gaccaccttgcagaaccgtggtctccttgtcacagtctaggcagcctct ggcttagcctctgtttctttcataacctttctcagcgcctgctctgggcc agaccagtgttgggaggagtcgctactgagctcctagattggcagggag gcagatggagaaaaggagtgtgtgtggtcagcattggagcagaggcagca gtgggcaatagaggaagtgagtaaatccttgggagggctccctagaagtg atgtgttttctttttttgttttagagacaggatctcgctctgtcgcccag gctggtgtgcagtggcatgatcatagctcactgcagcctcgacttctcgg gctcaagcaatcctcccacctcagcctcccaagtagctgggactacgggc acacgccaccatgcctggctaattttgtatttttgtagagatgggtct tcaccatgttgatcaggctggtctcgaactcctgggctcatgcgatccac cccgccagctgattacagggattccggtggtgagccaccgcgcccagacg ccacttcatcgtattgtaaacgtctgttacctttctgttccctgtctac tggactgtgagctccttagggccacgaattgaggatggggcacagagcaa gctctccaaacgttttgttgaatgagtgagggaatgaatgagttcaagcag atgctatacgttggctgttggagattttggctaaaatgggacttgcagga aagcccgacgtcccctcgccatttccaggcaccgctcttcagcttgggc tctgggtgagcgggatagggctgggtgcaggattaggataatgtcatggg tgaggcaagttgaggatggaagaggtggctgatggctgggctgtggaact gatgatcctgaaaagaagaggggacagtctctggaaatctaagctgaggc tgttgggggctacaggttgagggtcacgtgcagaagagaggctctgttct gaacctgcactatagaaaggtcagtgggatgcgggagcgtcggggcgggg
```
-continued
```
cggggcctatgttcccgtgtccccacgcctccagcaggggacgccgggc tgggggcggggagtcagaccgcgcctggtaccatccggacaaagcctgcg cgcgccccgcccgccattggccgtaccgccccgcgccgccgccccatcc cgcccctcgccgccgggtccggcgcgttaaagccaataggaaccgccgcc gttgttcccgtcacggacggggcagccaattgtggcggcgctcggcggct cgtggctctttcgcggcaaaaaggatttggcgcgtaaaagtggccgggac tttgcaggcagcggcggccgggggcggagcgggatcgagccctcgccgag gcctgccgccatgggcccgcgccgccgccgccgcctgtcaccgggccgc gcgggccgtgagcgtcatg
```

In some embodiments, the oncolytic virus (such as oncolytic adenovirus) comprises a viral vector comprising a tumor cell-specific promoter operably linked to a viral gene essential for replication of the oncolytic virus and a nucleic acid encoding an immune-related molecule (such as cytokine or chemokine) operably linked to a viral promoter. In some embodiments, the tumor-specific promoter is an E2F-1 promoter, such as a human E2F-1 promoter or an E2F-1 promoter comprising the nucleotide sequence set forth in SEQ ID NO:1. In some embodiments, the viral gene essential for replication of the oncolytic virus is selected from the group consisting of E1A, E1B, and E4. In some embodiments, the viral promoter operably linked to the nucleic acid encoding the immune-related molecule is the E3 promoter. In some embodiments, the immune-related molecule is GM-CSF.

In some embodiments, the oncolytic virus (such as oncolytic adenovirus) comprises a viral vector comprising a tumor cell-selective promoter operably linked to a viral gene essential for replication of the oncolytic virus and a nucleic acid encoding an immune-related molecule (such as cytokine or chemokine) operably linked to a viral promoter. In some embodiments, the tumor-selective promoter is an E2F-1 promoter, such as a human E2F-1 promoter or an E2F-1 promoter comprising the nucleotide sequence set forth in SEQ ID NO:1. In some embodiments, the viral gene essential for replication of the oncolytic virus is selected from the group consisting of E1A, E1B, and E4. In some embodiments, the viral promoter operably linked to the nucleic acid encoding the immune-related molecule is the E3 promoter. In some embodiments, the immune-related molecule is GM-CSF.

In some embodiments, the oncolytic virus is an adenovirus serotype 5, wherein the endogenous E1a promoter and E3 19 kD coding region of a native adenovirus is replaced by the human E2F-1 promoter and a nucleic acid encoding an immune-related molecule (such as cytokine or chemokine, for example, GM-CSF). In some embodiments, the tumor-specific promoter is a human E2F-1 promoter or an E2F-1 promoter comprising the nucleotide sequence set forth in SEQ ID NO:1.

In some embodiments, the oncolytic virus is CG0070, an adenovirus serotype 5 which has an E2F promoter at the E1a gene and a GM-CSF expression at the E3 gene.

CG0070 is a conditionally replicating oncolytic adenovirus (serotype 5) designed to preferentially replicate in and kill Rb pathway-defective cancer cells. This vector is transcriptionally regulated by a promoter (e.g., E2F-1 promoter) that is up-regulated in Rb-pathway-detective tumor cells. In approximately 85% of all cancers, one or more genes of the Rb pathway, such as the tumor suppressor Rb gene, are mutated. In addition to its restricted propagation, CG0070 also encodes the human cytokine GM-CSF, which is expressed selectively in the infected tumor cells to stimulate immune responses against uninfected distant (such as metastases) and local tumor foci.

The genomic structure of the oncolytic adenoviral vector CG0070 is shown schematically in FIG. 1. Products of the adenoviral early E1A gene are essential for efficient expression of other regions of the adenoviral genome. CG0070 has been engineered to express the E1A gene under control of the human E2F-1 promoter, which provides tumor specificity to the E1A gene product. To protect from transcriptional read-through activating E1A expression, a polyadenylation signal (PA) was inserted 5' of the E2F-1 promoter. CG0070 includes the entire wild type E3 region except for the 19 kD-coding region. A direct comparison of E3-containing to E3-deleted oncolytic adenovirus vectors showed superiority of E3-containing vectors in tumor spread and efficacy. In place of the 19 kD gene, CG0070 carries the cDNA for human GM-CSF under the control of the endogenous E3 promoter (E3P). Since the E3 promoter is in turn activated by E1A, both viral replication and GM-CSF expression are ultimately under the control of the E2F-1 promoter. The rest of the viral vector backbone, including the E2, E4, late protein regions and inverted terminal repeats (ITRs), is identical to the wild type Ad5 genome.

CG0070 is manufactured in HeLa-S3 cells, and released from infected HeLa-S3 cells by detergent lysis. CG0070 is purified from the lysate by chromatography, and then formulated in 5% sucrose, 10 mM Tris, 0.05% polysorbate-80, 1% glycine, 1 mM magnesium chloride, pH 7.8.

CG0070 is supplied as a sterile, slightly opalescent, frozen liquid in stoppered glass vials. The particle concentration per mL (vp/mL) is stated on the Certificate of Analysis for each lot of CG0070.

CG0070 has additional potential anti-tumor activity in that it carries the cDNA for human GM-CSF, a key cytokine for generating long-lasting anti-tumor immunity. Thus, CG0070 is a selectively replicating oncolytic vector with the potential for attacking the tumor by two mechanisms: direct cytotoxicity as a replicating vector and induction of a host immune response. In vitro and in vivo studies have been conducted to characterize the tumor selectivity and anti-tumor activity and safety of CG0070. See, for example, U.S. patent application publication No. US20150190505, which incorporated herein by reference in its entirety.

III. Pharmaceutical Compositions, Kits, and Articles of Manufacture

In another aspect, there are provided kits, unit dosages, and articles of manufacture useful for any one of the methods described herein.

In some embodiments, there is provided a pharmaceutical composition comprising an oncolytic virus (such as CG0070) and a pharmaceutically acceptable carrier, wherein the oncolytic virus comprises a viral vector comprising a tumor cell-specific promoter operably linked to a viral gene essential for replication of the oncolytic virus, and a heterologous gene encoding an immune-related molecule. The pharmaceutical composition may be used for treating bladder CIS (such as pure CIS) according to any one of the methods described herein.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. The final form may be sterile and may also be able to pass readily through an injection device such as a hollow needle. The proper viscosity may be achieved and maintained by the proper choice of solvents or excipients. The pharmaceutical carrier may include active or passive excipients for drug delivery, such as polymer and non-polymer systems. Other pharmaceutically acceptable carriers and their formulation are described in standard formulation treatises, e.g., Remington's Pharmaceutical Sciences by E. W. Martin.

The pharmaceutical compositions described herein may include other agents, excipients, or stabilizers to improve properties of the composition. Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. In some embodiments, the pharmaceutical composition is formulated to have a pH in the range of about 4.5 to about 9.0, including for example pH ranges of about any one of 5.0 to about 8.0, about 6.5 to about 7.5, or about 6.5 to about 7.0. In some embodiments, the pharmaceutical composition can also be made to be isotonic with blood by the addition of a suitable tonicity modifier, such as glycerol.

In some embodiments, there is provided a kit for treating bladder carcinoma in situ (such as pure CIS) in an individual, comprising an oncolytic virus (such as CG0070), wherein the oncolytic virus comprises a viral vector comprising a tumor cell-specific promoter operably linked to a viral gene essential for replication of the oncolytic virus, and a heterologous gene encoding an immune-related molecule. In some embodiments, the kit further comprises a pretreatment composition comprising a transduction enhancing agent, such as N-Dodecyl-β-D-maltoside (DDM). In some embodiments, the kit further comprises devices, materials, and/or instructions for carrying out any one of the methods described above. Medical device for intravesical delivery may include a catheter, for example, a Rusch 173430 Foley Catheter & BARD LUBRI-SIL Foley Catheter #70516SI.

The instructions relating to the use of the oncolytic virus (such as CG0070) generally include information as to dosage, dosing schedule, and route of administration for the intended treatment. The containers may be unit doses, bulk packages (e.g., multi-dose packages) or sub-unit doses. For example, kits may be provided that contain sufficient dosages of the oncolytic virus as disclosed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, 12 months or more. Kits may also include multiple unit doses of the oncolytic virus and instructions for use, packaged in quantities sufficient for storage and use in pharmacies, for example, hospital pharmacies and compounding pharmacies.

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container.

Suitable containers include, for example, bottles, vials, syringes, etc. The containers may be formed from a variety of materials such as glass or plastic. Generally, the container holds a composition which is effective for treating bladder CIS as described herein, and may have a sterile access port. The label or package insert indicates that the composition is used for treating the particular condition in an individual. The label or package insert will further comprise instructions for administering the composition to the individual. Articles of manufacture and kits comprising combination therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating bladder carcinoma in situ (such as pure CIS).

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The examples below are intended to be purely exemplary of the invention and should therefore not be considered to limit the invention in any way. The following examples and detailed description are offered by way of illustration and not by way of limitation.

Example 1: A Phase II Clinical Trial of CG0070 for Treating BCG-Unresponsive Non-Muscle-Invasive Bladder Cancer (NMIBC)

This example describes an open-label, single-arm, Phase II, multicenter study of the safety and efficacy of intravesical CG0070 monotherapy in patients with non-muscle invasive bladder carcinoma who have failed BG therapy and refused cystectomy. Most patients with NMIBC (Cis, Cis with Ta and/or T1, high grade Ta or T1 with frequent or uncontrolled recurrences) who have failed BCG intravesical therapy (standard of care) usually have no other choice but to proceed to cystectomy. Cystectomy is a surgery associated with major morbidity, mortality and quality of life issues. Morbidity and long term tedious medical care are associated with the rest of the patient's life span after cystectomy. Most patients at the NMIBC stages do not show signs of disease progression into the muscle layer or of metastasis, making surgery a very difficult decision. There is unmet need for therapeutic alternatives among this patient population.

CG0070 is a replication selective oncolytic adenovirus that destroys bladder tumor cells through their defective retinoblastoma (Rb) pathway. Prior reports of intravesical CG0070 have shown promising activity in patients with high-grade NMIBC who previously did not respond to BCG. However, limited accrual has hindered analysis of efficacy, particularly for pathologic subsets. Interim analysis at 6 months from the first intravesical administration of CG0070 was conducted to investigate the efficacy of CG0070 monotherapy in patients having bladder carcinoma in situ (CIS) with or without concurrent papillary carcinoma at Ta or T1 stage.

Experimental Design

In the study, each patient received intravesical CG0070 at a dose of $1\times10^{12}$ viral particles weekly for six weeks. Patients achieved a partial response or a complete response at 6 months post first intravesical intervention were maintained with the same treatment courses of six weekly intravesical instillation of CG0070. Patients were followed every 3 months for 24 months. At the 6-month follow up, patients were subjected to cystoscopy, urine cytology and biopsy. If no suspicious lesions were found, random biopsy of the bladder was obtained from the patients. Biopsy samples were reviewed by local and central pathologists, and treatment response was determined using both biopsy readings.

The primary outcome of the study measures durable complete response proportion (DCR) at the 18-month time point from the date of the first intravesical administration of CG0070. DCR is defined as the proportion of patients who experience a durable complete response lasting at least 6 months or longer (first interim analysis), at least 12 months or longer from the initial confirmed complete response date, and at least 18 months from the date of the first intravesical intervention. Secondary outcome measures include: cystectomy free survival at 18 months after the first intravesical treatment, complete response survival at 18 months after the first intravesical treatment, progression free survival at 18 months after the first intravesical treatment, time to progression to muscle invasive disease at 18 months after the first intravesical treatment, overall survival at 18 months and 24 months after the first intravesical treatment, PD-L1 status changes between pre-intervention and post intervention at either cystectomy or at biopsy up to 24 months, PD-L1 status of cancer cells and immune cells at tumor site by IHC, organ confined disease proportions at cystectomy, patient proportions with no cancer cells in regional lymph nodes at cystectomy, complete response proportions at 24 months after the first intravesical treatment, proportions of patients with a complete response of at least 12-month duration, disease regression proportions at 24 months after the first intravesical treatment, and proportions of patients with a partial response and/or a complete response of less than 12-month duration.

Patients must meet all of the following conditions to be eligible for the study:
1. 18 years of age or older, including adults and seniors;
2. Patients must have pathologically confirmed non-muscle invasive bladder cancer (NMIBC) high grade disease (HG), as defined by the 2004 WHO classification system;
3. Patients must have no evidence of muscle invasive disease;
4. Patients must be able to provide a sufficient biopsy sample to the central pathologist for histopathologically confirmed, transitional cell (urothelial) carcinoma. Urothelial tumors with mixed histology (but with <50% variant) are eligible;
5. Patients must have received at least two or more prior courses of intravesical therapy per recommended schedules. BCG must have been one of the prior therapies administered;
6. Patients can have either failed BCG induction therapy within a six-month period or have been successfully treated with BCG, but subsequently found to have recurrence. The first standard course of intravesical BCG therapy must include at least six weekly treatments (allowable range of instillations per course is 4-9). The second course of BCG therapy must include at least two weekly treatments;
7. Patients have either Cis or Cis with Ta and/or T1 disease at enrollment or in the past. For those patients with only Ta or T1 disease at enrollment AND with no history of Cis, they must have disease recurrence either must occur within 12 months of the most recent intravesical therapy of any kind, or disease recurrence within 18 months of BCG maintenance or disease recurrence within 24 months of BCG induction;
8. T1 patients need to have evidence of muscle included in their latest biopsy; and if not a re-TURBT has to be done prior to enrollment;

9. Radical cystectomy has been declined by the patient in a signed special section of the informed consent, whereby there is a clear explanation by the investigator to the subject that a delay of cystectomy may increase his/her chance of disease progression, the results of which may lead to serious and life threatening consequences;
10. Patients must be able to enter into the study within ten weeks of their most recent diagnostic procedure, which is usually a diagnostic biopsy, a transurethral resection of bladder tumor (TURBT) procedure or positive urine cytology;
11. Eastern Cooperative Oncology Group (ECOG) performance status <2;
12. Not pregnant or lactating;
13. Patients with child bearing potential must agree to use adequate contraception;
14. Agree to study specific informed consent and HIPAA authorization for release of personal health information; and
15. Adequate baseline CBC, renal and hepatic function. Parameters described as WBC>3000 cells/mm$^3$, ANC>1,000 cells/mm$^3$, hemoglobin >9.5 g/dL, and platelet count >100,000 cells/mm$^3$; Adequate renal function: serum creatinine <2.5 mg/dL; Bilirubin, AST and ALT not more than 2× Upper Limits of Normal; PT/INR, PTT, and fibrinogen within institutional acceptable limits; Absolute lymphocyte count ≥800/μL before the first dose of CG0070.

Patients who meet any of the following exclusion criteria are excluded from the study:
1. Previous systemic chemotherapy or radiation for bladder cancer. Note: Prior immunotherapy or intravesical (administered within the bladder) chemotherapy for superficial disease is acceptable;
2. History of anaphylactic reaction following exposure to humanized or human therapeutic monoclonal antibodies, hypersensitivity to GM-CSF or yeast derived products, clinically meaningful allergic reactions or any known hypersensitivity or prior reaction to any of the formulation excipients in the study drugs;
3. Known infection with HIV, HBV or HCV;
4. Anticipated use of chemotherapy or radiotherapy not specified in the study protocol while on study;
5. Any underlying medical condition that, in the Investigator's opinion, will make the administration of study vector hazardous to the patient, would obscure the interpretation of adverse events, or not permit adequate surgical resection;
6. Systemic treatment on any investigational clinical trial within 28 days prior to registration;
7. Concurrent treatment with immunosuppressive or immunomodulatory agents, including any systemic steroid (exception: inhaled or topically applied steroids, and acute and chronic standard dose NSAIDs, are permitted). Use of a short course (i.e., ≤1 day) of a glucocorticoid is acceptable to prevent a reaction to the IV contrast used for CT scans;
8. Immunosuppressive therapy, including: cyclosporine, antithymocyte globulin, or tacrolimus within 3 months of study entry;
9. History of prior experimental cancer vaccine treatment (e.g., dendritic cell therapy, heat shock vaccine) within the last year;
10. History of stage III or greater cancer, excluding urothelial cancer. Basal or squamous cell skin cancers must have been adequately treated and the subject must be disease-free at the time of registration. Subjects with a history of stage I or II cancer, must have been adequately treated and have been disease-free for ≥2 years at the time of registration;
11. Progressive or persistent viral or bacterial infection;
12. All infections must be resolved and the patient must remain afebrile for seven days without antibiotics prior to being placed on study;
13. Urinary tract infection, including particularly bladder infection, must be resolved prior to being placed on study; and
14. Unwilling or unable to comply with the protocol or cooperate fully with the investigator and site personnel.

Interim Analysis Results
Interim Analysis 1

At the interim analysis with an October 2016 cutoff date, thirty-six patients with residual high grade Ta, T1, or carcinoma in situ (CIS)+/−Ta/T1 had 6-month follow-up in this phase II single arm multicenter trial (NCT02365818). Inclusion criteria mandated receipt of at least 2 prior courses of intravesical therapy for CIS, with at least 1 of them being a course of BCG. Patients had either failed BCG induction therapy within 6 months or had been successfully treated with BCG with subsequent recurrence. Complete response (CR) at 6 months was defined as absence of disease on cytology, cystoscopy, and random biopsies.

Figure 2:
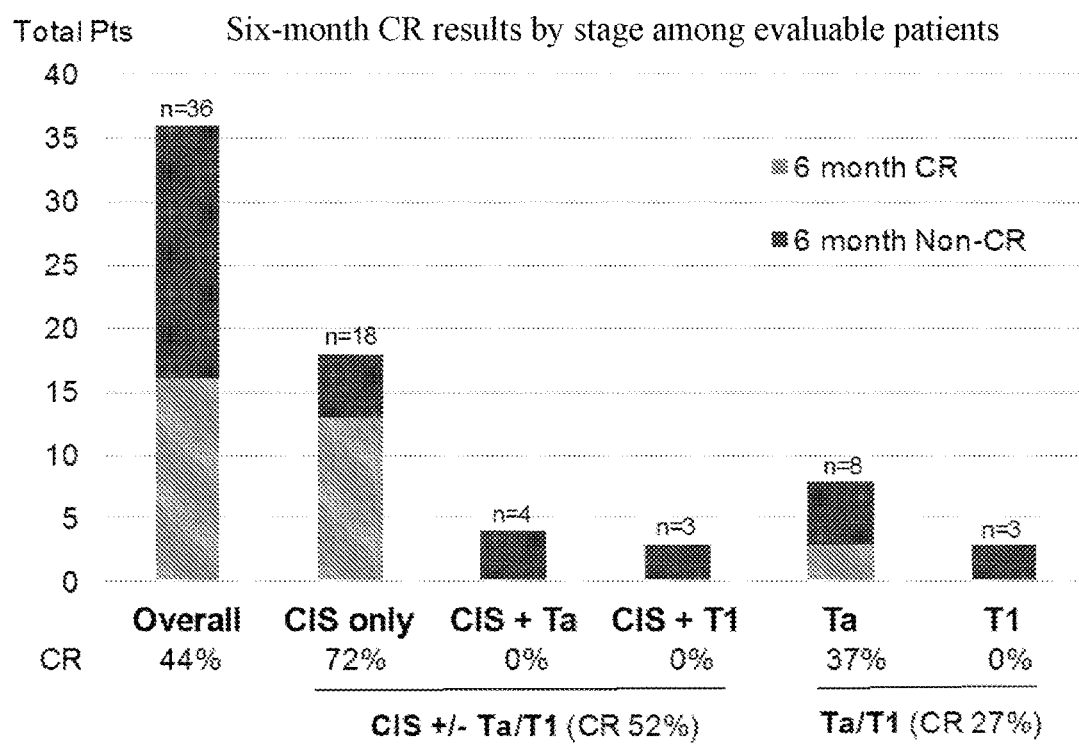
FIG. 2 shows percentage of complete response (CR) in patients having high-grade non-muscle-invasive bladder cancer of various stages at 6 months after receiving intravesical CG0070 therapy.

As shown in FIG. 2 and Table 1 below, among the 36 patients in this interim analysis, there were 18 CIS, 4 CIS+Ta, 3 CIS+T1, 8 Ta, and 3 T1. Overall 6 month CR was 44%. Notably, 6-month CR for patients with pure CIS was 72.2%, CIS+/−Ta/T1 52%, CIS+Ta/T1 0%, pure Ta/T1 27%. In non-responders with CIS, there were 4 patients (22%) with persistent CIS at 6 months, and 1 (5.6%) that progressed to CIS+T1. No patients with pure T1 or CIS+Ta/T1 had 6-month CR. In patients with both CIS+Ta/T1 (n=7), 5 had persistent Ta/T1+/−CIS, while 2 had CIS on biopsy at 6 months.

TABLE 1

6-month CR results among evaluable patients.

| Stage | No. CRs | % |
|---|---|---|
| CIS only (n=18) | 13 | 72 |
| CIS + Ta (n = 4) | 0 | 0 |
| CIS + T1 (n = 3) | 0 | 0 |
| CIS + Ta/T1 (n = 25) | 13 | 52 |
| Ta (n = 8) | 3 | 37 |
| T1 (n = 3) | 0 | 0 |
| Ta/T1 (n = 11) | 3 | 27 |
| Overall CR Rate (n = 36) | 16 | 44 |

All treatment related adverse events (AEs) at 6 months were Grade 1-3, most commonly urinary: dysuria (47%), bladder spasms (44%), hematuria (36%), and urgency (33%). Immunologic treatment related AEs included fatigue (11%) and chills (5.6%). Grade 3 treatment related AEs included dysuria (5.6%) and hypotension (2.7%). There were no Grade 4/5 treatment related AEs.

Interim Analysis 2

6-month clinical response results at the interim analysis with an Apr. 14, 2017 cutoff date are summarized in Tables 2-5.

Patients with no evidence of malignancy according to either pathology or urine cytology examination, or in most recent pathology examination were disqualified for the study. To determine the baseline stage of each patient, patient samples were evaluated by a local pathologist and a central pathologist. If the local pathologist and the central pathologist did not agree, but both found malignancy, then the stages determined by both local and central pathologists were combined. If the local pathologist and the central pathologist did not agree and only one found malignancy, then the patient was considered to have malignancy using the stage determined by the pathologist who found malignancy. If the patient samples were only evaluated by either the local pathologist or the central pathologist, then the single available reading was used. If neither pathologist found malignancy, but urine cytology was positive, then the stage of the patient was annotated as "unknown." If neither pathologist found malignancy, but urine cytology was absent or negative, then the stage of the patient was annotated as "negative." Pathology reports with "papillary" were entered as Ta+T1. Pathology reports with "High grade UCC" was interpreted as "Ta", unless invasion into lamina propria (T1) or lamina muscularis (T2) was identified. If urine cytology was the only method of evaluation, and the result was atypical or suspicious, and there was no pathological report, then the stage was annotated as "negative." If urine cytology was the only method of evaluation and a second urine cytology result was negative, then the time point was considered negative.

Clinical response of the patients was determined using the same staging rules as for the baseline stage assessment described above. Patients with complete response (CR) include those who were assessed as "negative" at 6 month following CG0070 treatment. Patients with progressive disease (PD) include those who had prior time point assessment as "negative" and current time point assessment as not "negative," and those who had progression to T2 or higher stage.

TABLE 2

Complete Response (CR) Rate Based on Stage in Intent to Treat (ITT) Population (n = 67*) at 6 Months

| Stage | No. CRs | % |
| --- | --- | --- |
| CIS (n = 31) | 14 | 45.2 |
| CIS + Ta/T1 (n = 16) | 4 | 25.0 |
| CIS-Containing (n = 47) | 18 | 38.3 |
| Ta/T1 (n = 19) | 3 | 15.8 |
| Unknown (n = 1) | 0 | 0 |
| All (n = 67) | 21 | 31.3 |

*22 of 67 patients considered Not Evaluable (NE) at 6 months and assumed not to have a CR

TABLE 3

Overall Response at 6 Months in ITT Population (n = 67)

| Response | No. Patients | % |
| --- | --- | --- |
| CR | 21 | 31.3 |
| Non-CR (SD + Regression) | 12 | 17.9 |
| PD | 12 | 17.9 |
| NE | 22 | 32.8 |

TABLE 4

Complete Responses (CRs) Based on Stage in Patients Achieving 6 Month Evaluation (n = 45)

| Stage | No. CRs | % |
| --- | --- | --- |
| CIS (n = 24) | 14 | 58.3 |
| CIS + Ta/T1 (n = 12) | 4 | 33.3 |

TABLE 4-continued

Complete Responses (CRs) Based on Stage in Patients Achieving 6 Month Evaluation (n = 45)

| Stage | No. CRs | % |
| --- | --- | --- |
| CIS-Containing (n = 36) | 18 | 50 |
| Ta/T1 (n = 9) | 3 | 33.3 |
| All (n = 45) | 21 | 46.7 |

TABLE 5

Overall Response in Patients Achieving 6 Month Evaluation (n = 45)

| Response | No. Patients | % |
| --- | --- | --- |
| CR | 21 | 46.7 |
| Non-CR (SD + Regression) | 12 | 26.7 |
| PD | 12 | 26.7 |

This phase II study demonstrates that intravesical CG0070 yielded an overall 46.7% complete response rate at 6 months with an acceptable level of toxicity for patients with high-risk BCG-unresponsive NMIBC. There is a particularly strong response and limited progression in patients with pure CIS. Ongoing follow-up for this study will be valuable in the BCG-unresponsive NMIBC population.

Final Results

A total of 67 patients having CIS, CIS+Ta, CIS+T1, Ta, or T1 stage bladder cancer were treated with intravesical CG0070. Patients were evaluated at 6 and 12 months for complete response, as described above. Table 7 shows the response rate to CG0070 for patients with BCG unresponsive, BCG refractory, and BCG relapsing bladder cancer. BCG unresponsive patients shows a 49% complete response rate at 6 months and a 30% complete response rate at 12 months. BCG refractory patients showed a 56% complete response rate at 6 months and a 44% complete response rate at 12 months. Finally, BCG relapsing patients showed a 35% response rate at 6 months and an 18% response rate at 12 months. This demonstrates that CG0070 is effective for treating BCG unresponsive, BCG relapsing, and BCG refractory patients.

TABLE 6

Cancer Stage of Patients Evaluated

| Cancer Stage | |
| --- | --- |
| CIS alone (N = 31) | 46% |
| CIS + Ta (N = 11) | 16% |
| CIS + T1 (N = 4) | 6% |
| CIS Ta T1 (N = 2) | 3% |
| Ta (N = 11) | 16% |
| T1 (N = 6) | 9% |
| Ta, T1 (N = 2) | 3% |

TABLE 7

Response Rate after 6 and 12 months

| | N | Proportion | # CR @ 6 Months | CR @ 6 Months | # CR @ 12 Months | CR @ 12 Months |
| --- | --- | --- | --- | --- | --- | --- |
| BCG Unresponsive (0-6, 6-12) | 43 | 64% | 21 | 49% | 13 | 30% |
| BCG Refractory (0-6) | 27 | 40% | 15 | 56% | 12 | 44% |
| BCG Relapsing (6-12, 12+) | 34 | 51% | 12 | 35% | 6 | 18% |
| Insufficient Data | 6 | 9% | 2 | 33% | 0 | 0% |

Responsiveness of patients with BCG unresponsive bladder cancer was also analyzed by cancer subtype, as summarized in Table 8. As shown in Table 8, patients with papillary cancers showed a somewhat higher complete response rate than patients with CIS-containing cancers (62% vs 46% CR at 6 months and 55% vs 26% CR at 12 months).

TABLE 8

Complete Response Rates in BCG Unresponsive Sub Populations.

|  | 6 Month | | 12 Month | |
| --- | --- | --- | --- | --- |
|  | # CR @ 6 Months | CR @ 6 Months | # CR @ 12 Months | CR @ 12 Months |
| CIS alone | 8 | 53% | 3 | 21% |
| CIS + Ta | 4 | 50% | 4 | 50% |
| CIS + T1 | 0 | 0% | 0 | 0% |
| CIS + Ta + T1 | 1 | 50% | 0 | 0% |
| Total Cis-containing | 13 | 46% | 7 | 26% |
| Ta | 4 | 67% | 2 | 50% |
| T1 | 4 | 80% | 4 | 80% |
| Ta + T1 | 0 | 0% | 0 | 0% |
| Total papillary | 8 | 73% | 6 | 75% |
| Total BCG Unresponsive | 21 | 54% | 13 | 36% |

The association between time to relapse and responsiveness to CG0700 therapy was also evaluated. Out of 14 counted subjects that relapsed after achieving a CR, 64% (9/14) relapsed at 6-month after achieving CR at 3-month. CR is sustainable starting at 9-month if relapse does not occur after this timepoint. No Ta/T1 patients relapsed after achieving CR.

In summary, this phase II study of CG0700 demonstrates its effectiveness for treating both CIS-containing and papillary bladder cancer. Patients with unresponsive, BCG refractory, and BCG relapsing bladder cancer all showed high response rates to CG0700 demonstrating its efficacy in these underserved patient groups. The high level of efficacy of the CG0700 therapy suggests that it could be a viable alternative to radical cystectomy, allowing patients with non-muscle invasive bladder cancer to preserve their bladders and increasing the quality of life for these patients.

Example 2: Phase III Clinical Trial of CG0070 for Treatment of Patients with Bladder Cancer This study shows the effect of a treatment regimen with CG0070 comprising an induction phase and a maintenance phase. Patients with bladder cancer are administered CG0700 therapy once per week for six weeks at month 0 during an induction phase. At month three, patients are reassessed. Patients with persistent disease will continue the induction therapy and receive a weekly CG0070 for six weeks at three months. Patients who show a complete response will begin a maintenance phase and receive weekly CG0070 for three weeks at three months. At month 6, all patients will receive CG0070 weekly for three weeks in a maintenance phase. At months 12 and 18, patients will receive CG0070 weekly for three weeks during the maintenance phase. Patients will receive a maximum of 21 doses of CG0700. Complete response rate is assessed.

Example 3: Treatment of Patients with Ta or T1 Non-Muscle Invasive Bladder Cancer Who have not Received TURBT This study shows the effect of treatment of patients with Ta or T1 non-muscle invasive bladder cancer who have not received a transurothelial resection of bladder tumor (TURBT), for example in a neoadjuvant setting. Patients who have not received a TURBT are administered CG0070. Patients include those who are ineligible for TURBT and patients who are considered to have non-resectable Ta or T1 stage bladder cancer. Complete response rate is assessed.

What is claimed is:

1. A method of treating bladder cancer in an individual or preserving bladder in an individual, comprising intravesically administering to the individual an effective amount of an oncolytic virus once per week for six weeks during an induction phase, and subsequently administering to the individual an effective amount of the oncolytic virus once per week for three weeks every six months during a maintenance phase, wherein the start of the induction phase and the start of the maintenance phase are separated by about 3 months or about 6 months, and wherein the oncolytic virus comprises a viral vector comprising a tumor cell-specific promoter operably linked to a viral gene essential for replication of the oncolytic virus, and a heterologous gene encoding an immune-related molecule.

2. The method of claim 1, wherein the start of the induction phase and the start of the maintenance phase are separated by about 3 months.

3. The method of claim 1, wherein the start of the induction phase and the start of the maintenance phase are separated by about 6 months.

4. The method of claim 1, wherein the induction phase comprises administering to the individual an effective amount of the oncolytic virus once per week for six weeks on month zero and month three of a treatment regimen.

5. The method of claim 1, wherein the individual has Ta or T1 stage bladder cancer.

6. The method of claim 1, wherein the individual is unresponsive to BCG treatment or has disease reoccurrence subsequent to BCG treatment.

7. The method of claim 1, wherein the individual has not received a cystectomy.

8. The method of claim 1, wherein the oncolytic virus is CG0070.

9. The method of claim 1, wherein the oncolytic virus is administered at a dose of about $1 \times 10^8$ to about $1 \times 10^{14}$ viral particles.

10. The method of claim 1, further comprising intravesically administering to the individual a transduction enhancing agent prior to the administration of the oncolytic virus.

11. The method of claim 1, wherein the oncolytic virus is administered as a single therapeutic agent.

12. The method of claim 5, wherein the individual does not have carcinoma in situ.

13. The method of claim 1, wherein the individual has carcinoma in situ.

14. The method of claim 13, wherein the individual has Ta or T1 stage bladder cancer.

15. The method of claim 13, wherein the individual does not have a concurrent papillary carcinoma of Ta or T1 stage.

16. The method of claim 6, wherein the individual has failed BCG treatment within about 6 months.

17. The method of claim 6, wherein the individual has failed BCG treatment within about 12 months after the last administration of BCG.

18. The method of claim 1, wherein the tumor cell specific promoter is an E2F-1 promoter.

19. The method of claim 1, wherein the immune related molecule is GM-CSF.

20. The method of claim 1, wherein the oncolytic virus is an oncolytic adenovirus.

21. The method of claim 20, wherein the oncolytic virus is an adenovirus serotype 5, wherein the endogenous E1a promoter of the native adenovirus serotype 5 is replaced by the human E2F-1 promoter, and the endogenous E3 19 kD coding region of the native adenovirus serotype 5 is replaced by a nucleic acid encoding human GM-CSF.

* * * * *

UNITED STATES PATENT AND TRADEMARK OFFICE
CERTIFICATE OF CORRECTION

| | | |
|---|---|---|
| PATENT NO. | : 11,338,003 B2 | Page 1 of 1 |
| APPLICATION NO. | : 16/605066 | |
| DATED | : May 24, 2022 | |
| INVENTOR(S) | : Arthur Kuan | |

It is certified that error appears in the above-identified patent and that said Letters Patent is hereby corrected as shown below:

On the Title Page

In the References Cited:
Column 2, in the OTHER PUBLICATIONS section, in the clinicaltriais.gov (Sep. 2011) reference, please replace "Clinica1Trials.gov" with --ClinicalTrials.gov--.
On page 2, Column 1, in the OTHER PUBLICATIONS section, in the Lamm D. et. al. (2006) reference, please replace "/V9046" with --/V0046--.
On page 2, Column 1, in the OTHER PUBLICATIONS section, in the Packiam, V. T. et al. (Oct. 2018, e-pub Jul. 26, 2017) reference, please replace "Muscie" with --Muscle--.

In the Specification

At Column 15, Line number 48, please replace "MEW" with --MHC--.
At Column 16, Line number 24, please replace "Fresolumimab)." with --Fresolimumab).--.
At Column 18, Line number 6, please replace "0 is," with --0is,--.
At Column 19, Line number 51, please replace "phososensitizer," with --photosensitizer,--.
At Column 29, Line number 21, please replace "$1 \times 10^{'4}$" with --$1 \times 10^{14}$--.
At Column 34, Line number 35, please replace "Mill" with --MRI--.
At Column 34, Line number 59, please replace "laherparapvec" with --laherparepvec--.

In the Claims

At Column 48, Claim number 9, Line number 30, please replace "$1 \times 10^{14}$" with --$1 \times 10^{14}$--.

Signed and Sealed this
Twenty-fourth Day of January, 2023

Katherine Kelly Vidal
*Director of the United States Patent and Trademark Office*

SEQUENCE LISTING

```
<160> NUMBER OF SEQ ID NOS: 1

<210> SEQ ID NO 1
<211> LENGTH: 1519
<212> TYPE: DNA
<213> ORGANISM: Artificial Sequence
<220> FEATURE:
<223> OTHER INFORMATION: Synthetic Construct

<400> SEQUENCE: 1
gggcccaaaa ttagcaagtg accacgtggt tctgaagcca gtggcctaag gaccacccct      60
gcagaaccgt ggtctccttg tcacagtcta ggcagcctct ggcttagcct ctgtttcttt     120
cataaccttt ctcagcgcct gctctgggcc agaccagtgt tgggaggagt cgctactgag     180
ctcctagatt ggcaggggag gcagatggag aaaaggagtg tgtgtggtca gcattggagc     240
agaggcagca gtgggcaata gaggaagtga gtaaatcctt gggagggctc cctagaagtg     300
atgtgttttc ttttttttgtt ttagagacag gatctcgctc tgtcgcccag gctggtgtgc     360
agtggcatga tcatagctca ctgcagcctc gacttctcgg gctcaagcaa tcctcccacc     420
tcagcctccc aagtagctgg gactacgggc acacgccacc atgcctggct aattttttgta     480 ttttttgtag agatgggtct tcaccatgtt gatcaggctg gtctcgaact cctgggctca     540
tgcgatccac cccgccagct gattacaggg attccggtgg tgagccaccg cgcccagacg     600
ccacttcatc gtattgtaaa cgtctgttac ctttctgttc ccctgtctac tggactgtga     660
```

-continued

```
gctccttagg gccacgaatt gaggatgggg cacagagcaa gctctccaaa cgtttgttga    720
atgagtgagg gaatgaatga gttcaagcag atgctatacg ttggctgttg gagattttgg    780
ctaaaatggg acttgcagga aagcccgacg tccccctcgc catttccagg caccgctctt    840
cagcttgggc tctgggtgag cgggataggg ctgggtgcag gattaggata atgtcatggg    900
tgaggcaagt tgaggatgga agaggtggct gatggctggg ctgtggaact gatgatcctg    960
aaaagaagag gggacagtct ctggaaatct aagctgaggc tgttgggggc tacaggttga   1020
gggtcacgtg cagaagagag gctctgttct gaacctgcac tatagaaagg tcagtgggat   1080
gcgggagcgt cggggcgggg cggggcctat gttcccgtgt ccccacgcct ccagcagggg   1140
acgcccgggc tggggcggg gagtcagacc gcgcctggta ccatccggac aaagcctgcg   1200
cgcgccccgc cccgccattg gccgtaccgc cccgcgccgc cgcccatcc cgcccctcgc    1260 cgccgggtcc ggcgcgttaa agccaatagg aaccgccgcc gttgttcccg tcacggacgg   1320
ggcagccaat tgtggcggcg ctcggcggct cgtggctctt tcgcggcaaa aaggatttgg   1380
cgcgtaaaag tggccgggac tttgcaggca gcggcggccg ggggcggagc gggatcgagc   1440
cctcgccgag gcctgccgcc atgggcccgc gccgccgccg ccgcctgtca cccgggccgc   1500
gcgggccgtg agcgtcatg                                                1519
```